United States Patent [19]
Bonin

[11] Patent Number: 5,661,235
[45] Date of Patent: Aug. 26, 1997

[54] MULTI-DIMENSIONAL CAPACITIVE TRANSDUCER

[75] Inventor: Wayne A. Bonin, North Oaks, Minn.

[73] Assignee: Hysitron Incorporated, Minneapolis, Minn.

[21] Appl. No.: 579,996

[22] Filed: Dec. 20, 1995

Related U.S. Application Data

[63] Continuation-in-part of Ser. No. 337,741, Nov. 14, 1994, Pat. No. 5,576,483, which is a continuation-in-part of Ser. No. 327,979, Oct. 24, 1994, Pat. No. 5,553,486, which is a continuation-in-part of Ser. No. 131,405, Oct. 1, 1993, abandoned.

[51] Int. Cl.$^6$ .................................................... G01B 5/28
[52] U.S. Cl. .................... 73/105; 73/862.626; 361/283.2; 361/283.3; 361/283.4
[58] Field of Search .................................. 73/105, 98, 81, 73/82, 718, 720, 724, 862.626, 862.043, 862.041, 862.68, 862.628, 862.042; 361/271, 280, 281, 283.1, 283.2, 283.3, 283.4; 177/210 C

[56] References Cited

U.S. PATENT DOCUMENTS

| | | | |
|---|---|---|---|
| 3,307,407 | 3/1967 | Berg et al. | 73/432 |
| 3,314,493 | 4/1967 | Kennedy | 177/210 |
| 3,418,546 | 12/1968 | Beavers et al. | 317/246 |
| 4,040,118 | 8/1977 | Johnston | 361/283 |
| 4,089,036 | 5/1978 | Geronime | 361/283 |
| 4,196,632 | 4/1980 | Sikorra | 73/718 |
| 4,237,989 | 12/1980 | Lewis | 177/210 |
| 4,294,321 | 10/1981 | Wittlinger et al. | 177/210 FP |
| 4,310,806 | 1/1982 | Ogasawara | 331/40 |
| 4,479,392 | 10/1984 | Froeb et al. | 73/862.68 |
| 4,523,473 | 6/1985 | Chamuel | 73/643 |
| 4,523,474 | 6/1985 | Browne et al. | 73/724 |
| 4,550,617 | 11/1985 | Fraignier et al. | 73/862.04 |
| 4,685,678 | 8/1987 | Frederiksen | 273/148 |
| 4,694,687 | 9/1987 | Bonin et al. | 73/116 |

(List continued on next page.)

FOREIGN PATENT DOCUMENTS

| | | |
|---|---|---|
| 1-195338 | 8/1989 | Japan. |
| 2-231546 | 9/1990 | Japan. |
| 2 189 607 | 10/1987 | United Kingdom. |
| WO88/00691 | 1/1988 | WIPO. |

OTHER PUBLICATIONS

Wickramasinghe, "Scanned–Probe Microscopes", *Scientific American*, Oct., 1989, pp. 98–105.

Grigg, et al., "Tip–sample forces in scanning microscopy in air and vacuum", *J. Vac. Sci. Technol. A*, vol. 10, No. 4, Jul./Aug., 1992, pp. 680–683.

Heerens, "Application of capacitance techniques in sensor design", *J. Phys. E. Sci. Instrum.*, vol. 19, 1986, pp. 897–906.

Nishibori et al., "Ultra–Microhardness of Vacuum–Deposited in Ultra–Microhardness Tester", *Thin Solid Films*, vol. 48, 1978, pp. 325–331.

Tsukamoto et al., "Mechanical Properties of Thin Films measurements of Ultramicroindentation Hardness Young's Modulus and Internal Stress".

Yanagisawa et al., "An Ultramicro Indentation Hardness Tester and Its Application to Thin Films", *Lubrication Engineering*, vol. 45, Jan., 1987, pp. 52–56.

(List continued on next page.)

*Primary Examiner*—Michael Brock
*Assistant Examiner*—Daniel S. Larkin
*Attorney, Agent, or Firm*—Nawrocki, Rooney & Sivertson, P.A.

[57] ABSTRACT

High precision force imparting and/or a force (including weight) and displacement measuring/indicating device which includes a multi-dimensional capacitor transducer system. The multi-dimensional transducer includes a first capacitive transducer for imparting force or movement and/or detecting force, weight or position in a first direction and a second capacitive transducer for imparting force or movement and/or detecting force, weight or position in a second direction. The multi-dimensional transducer may be used to provide in situ imaging in micro-mechanical test systems.

34 Claims, 16 Drawing Sheets

U.S. PATENT DOCUMENTS

| | | | |
|---|---|---|---|
| 4,699,000 | 10/1987 | Lashmore et al. | 73/81 |
| 4,750,082 | 6/1988 | Gerety | 361/283 |
| 4,820,051 | 4/1989 | Yanagisawa et al. | 356/378 |
| 4,848,141 | 7/1989 | Oliver et al. | 73/81 |
| 4,922,444 | 5/1990 | Baba | 364/566 |
| 4,970,374 | 11/1990 | Ueda et al. | 219/518 |
| 5,006,952 | 4/1991 | Thomas | 361/283 |
| 5,065,103 | 11/1991 | Slinkman et al. | 324/458 |
| 5,083,091 | 1/1992 | Frick et al. | 324/678 |
| 5,092,174 | 3/1992 | Reidmeister et al. | 73/517 |
| 5,115,291 | 5/1992 | Stokes | 357/26 |
| 5,128,671 | 7/1992 | Thomas, Jr. | 341/20 |
| 5,134,886 | 8/1992 | Ball | 73/718 |
| 5,174,159 | 12/1992 | Jacobsen et al. | 73/767 |
| 5,193,383 | 3/1993 | Burnham et al. | 73/105 |
| 5,255,562 | 10/1993 | Yamamoto et al. | 73/160 |
| 5,305,633 | 4/1994 | Weissenbacher et al. | 73/82 |
| 5,359,879 | 11/1994 | Oliver et al. | 73/7 |
| 5,381,300 | 1/1995 | Thomas et al. | 361/280 |
| 5,383,364 | 1/1995 | Takahashi et al. | 73/517 R |
| 5,412,327 | 5/1995 | Meinen | 324/686 |
| 5,421,213 | 6/1995 | Okada | 73/862.043 |
| 5,424,650 | 6/1995 | Frick | 324/688 |
| 5,437,196 | 8/1995 | Okada | 73/862 |
| 5,492,020 | 2/1996 | Okada | 73/862 |

OTHER PUBLICATIONS

Newey et al., "An Ultra–low–load penetration hardness tester", *J. Phys. E. Sci. Instrum.*, vol. 15, 1982, pp. 119–122.

Wierenga et al., "Ultramicroindentation apparatus for the mechanical characterization of thin films", *J. Appl. Phys.*, vol. 55, No. 12, Jun. 15, 1984, pp. 42244–42247.

Wierenga et al., "Ultramicrohardness Experiments on Vapour–Deposited Films of Pure Metals and Alloys", *Thin Solid Films*, vol. 119, 1984, pp. 375–382.

Burnham et al., "Measuring the nanomechanical properties and surface forces of materials using an atomic force microscope", *J. Vac. Sci. Technol. A*, vol. 7, No. 4, Jul./Aug., 1989, pp. 2906–2913.

Oliver et al., "Thin Film Characterization Using a Mechanical Properties Microprobe", *Thin Solid Films*, vol. 153, 1987, pp. 185–96.

Wu, "Microscratch and load relaxation tests for ultra–thin films", *J. Mater. Res.*, vol. C, No. 2, Feb., 1991, pp. 407–426.

Holman et al., "Using capacitive sensors for in situ calibration of displacements in a piezo–driven translation stage of an STM", *Sensors and Actuators A*, vol. 36, 1993, pp. 37–42.

Weihs et al., "Mechanical deflection of cantilever microbeams: A new technique for testing the mechanical properties of thin films", *J. Mater. Res.*, vol. 3, No. 5, Sep./Oct. 1988, pp. 931–942.

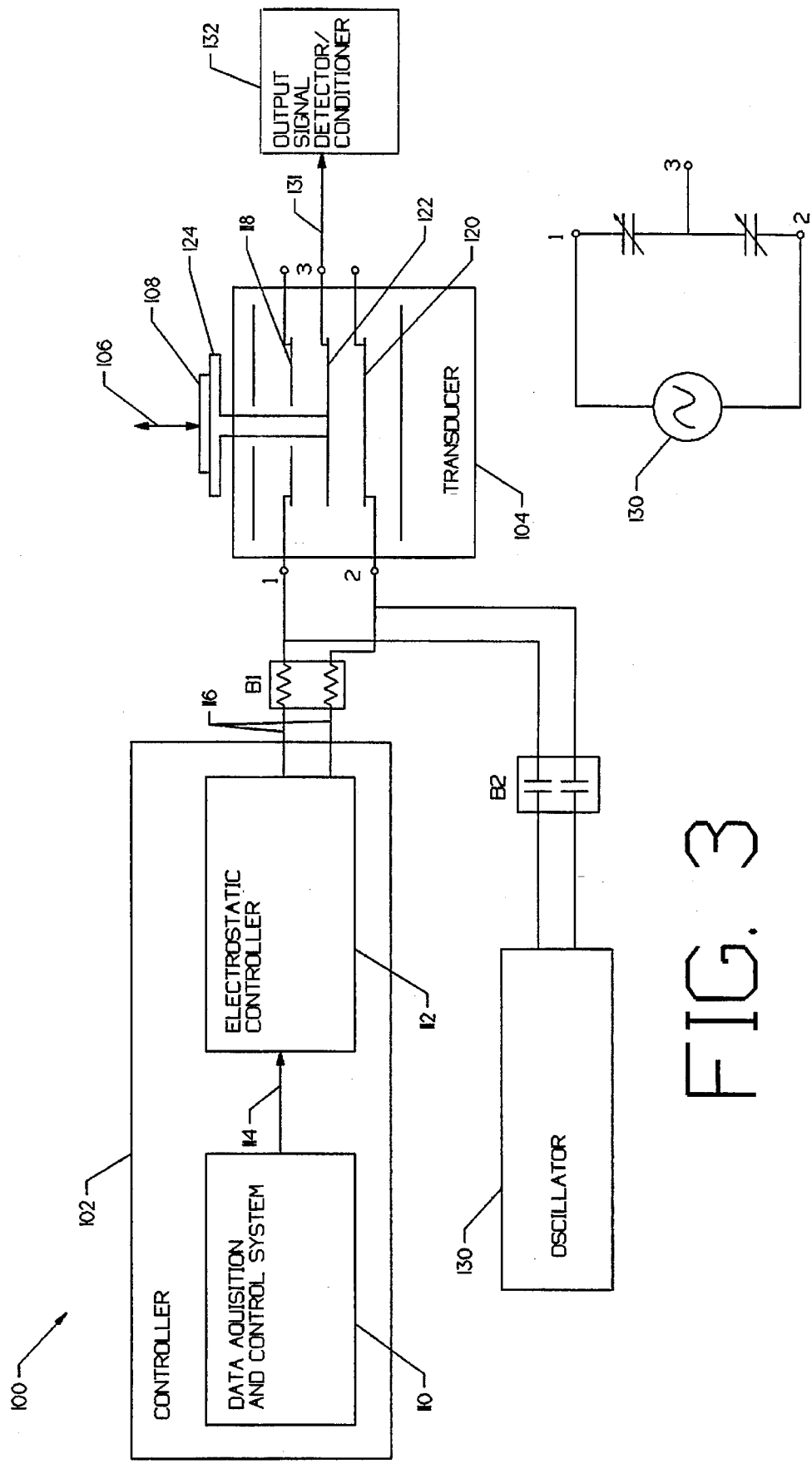

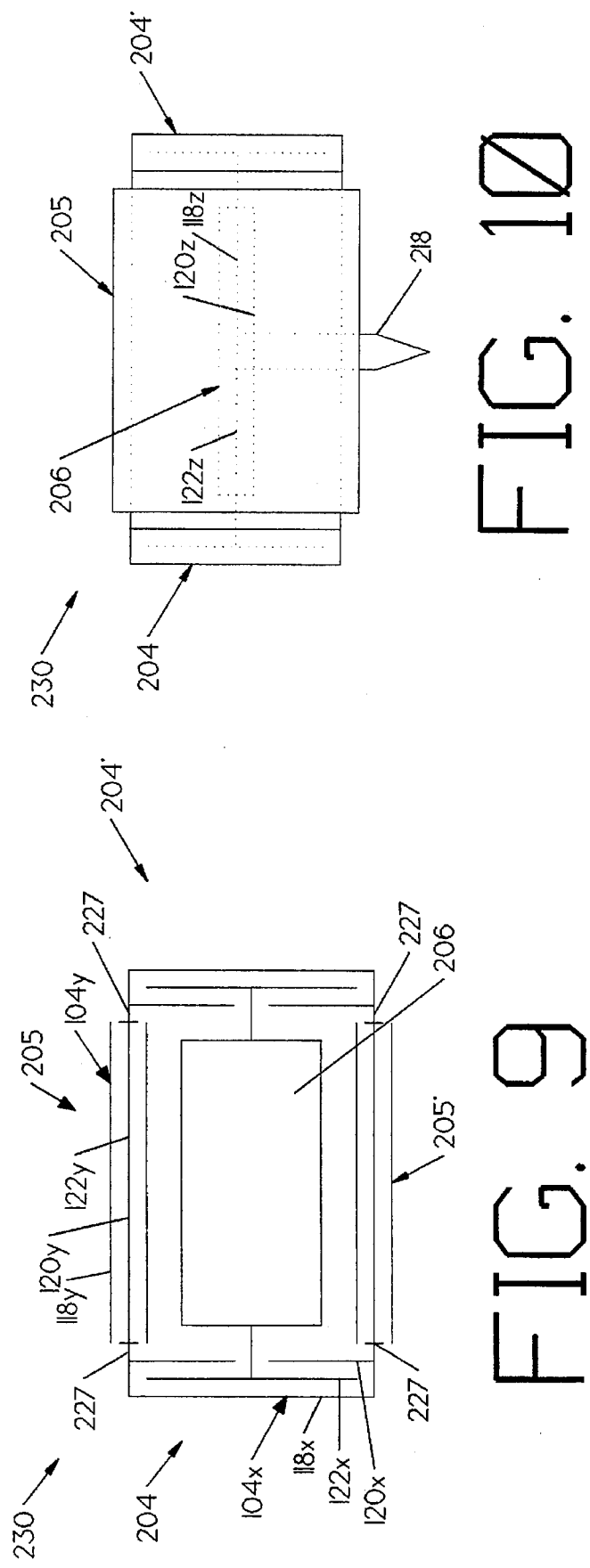

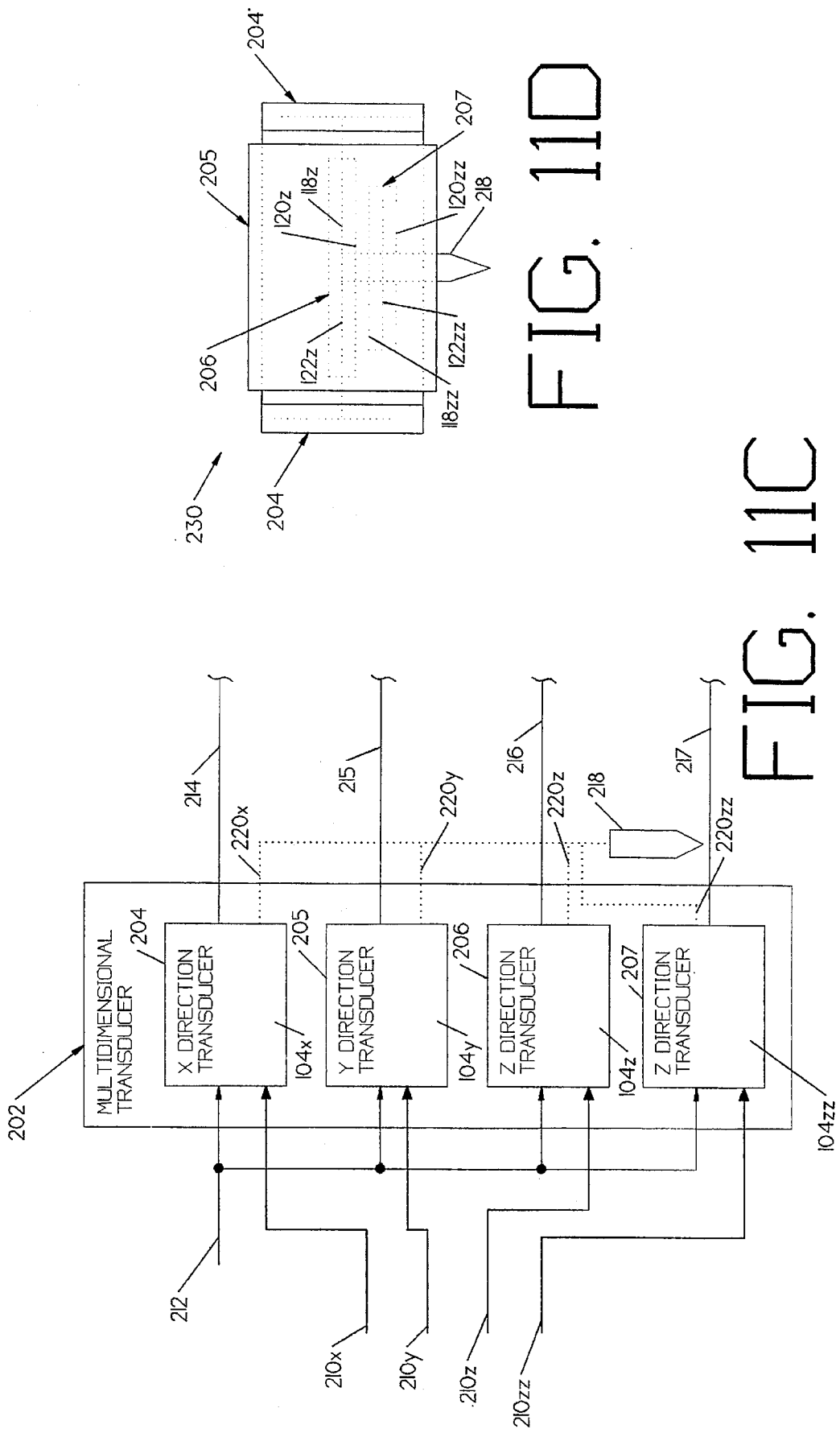

MULTI-DIMENSIONAL CAPACITIVE TRANSDUCER

RELATED APPLICATIONS

The present application is a continuation-in-part of application. Ser. No. 08/337,741, filed Nov. 14, 1994, now U.S. Pat. No. 5,576,483, which is a continuation-in-part of Ser. No. 08/327,979, filed Oct. 24, 1994, now U.S. Pat. No. 5,553,486 which is a continuation-in-part of U.S. Ser. No. 08/131,405, filed on Oct. 1, 1993, now abandoned. To the extent that disclosure of the above earlier filed applications are not completely contained herein, those applications are hereby incorporated by reference.

TECHNICAL FIELD

The present invention relates to high precision sensor systems. More particularly, it is directed to high precision force imparting and/or force (including weight) and displacement measuring/indicating transducers which include a multi-plate capacitor system. Additionally, it is directed to devices incorporating such a transducer.

BACKGROUND OF THE INVENTION

Many applications for precise measurement of force, weight, and relative position are known in the art. For example, machine shop tools for precisely indicating or fabricating holes, channels or other surface features relative to one another require accurate position or displacement measurement. Accurate measurement of displacement or position on small parts, such as those used in the manufacture of electronic components is particularly important.

Measurement of force or weight accurately at minute quantities, along with instruments to accomplish such measurements are well known. Strain gauge transducers are one industry recognized instrument for such measurements. These instruments can be used in laboratory analysis, such as micro hardness testing of samples. Furthermore, laboratory scales for measuring constituent components in minute quantities with high resolution are well known in chemical, biological, drug and medical fields.

A known limitation to resolution in strain gauge transducers is the signal to noise ratio of the instrument. Strain gauge transducers have an output of only a few millivolts. It is recognized that the minimal possible noise level for the strain gauge transducer is set by the thermal noise on the strain gauge resistive element. For example, the calculated noise for a commercial strain gauge sensor with 350 Ohm resistance is 2.4 nV at 1 Hz bandwidth.

In more recent years, the development of scanned-probe microscopes has created a need for higher resolution measurement of force and position at minute levels. As disclosed by Wickramasinghe in "Scanned-Probe Microscopes", *Scientific American*, October, 1989, pp. 98–105, scanned-probe microscopes allow an examination of a surface at very close range with a probe that may be just a single atom across, and resolve features and properties on a scale that eludes other microscopes.

The disclosure of Wickramasinghe, which is incorporated herein by reference, discloses two types of scanned-probe microscopes. The first type is a scanning tunneling microscope, while the second is an atomic force microscope.

In the atomic force microscope, a scanned-probe device moves a minute tip, such as an atomically sharp diamond mounted on a metal foil over a specimen in a raster pattern. The instrument records contours of force, the repulsion generated by the overlap of the electron cloud at the tip with the electron clouds of surface atoms. In effect, the tip, like the stylus of a phonograph, reads the surface. The foil acts as a spring, keeping the tip pressed against the surface as it is jostled up and down by the atomic topography.

A scanning tunneling microscope senses atomic-scale topography by means of electrons that tunnel across the gap between a probe and the surface. Piezoelectric ceramics, which change size slightly in response to changes in applied voltage, maneuver the tungsten probe of a scanning tunneling microscope in three dimensions. A voltage is applied to the tip, and is moved toward the surface, which must be conducting or semiconducting, until a tunneling current starts to flow. The tip is then scanned back and forth in a raster pattern. The tunneling current tends to vary with the topography. A feedback mechanism responds by moving the tip up and down, following the surface relief. The tip's movements are translated into an image of the surface.

With scanning tunneling microscopy, it is recognized that measurement of surface topography would be incorrect if the tip distance from the surface is not maintained. Thus, a measurement of the force applied by the tip on the sample throughout the measurement cycle would serve to confirm that such distance is maintained, and provide a cross-check for the accuracy of the topographic measurement.

As previously stated, instruments such as strain gauge transducers can be used for micro hardness testing of samples while scanning tunneling microscopes and atomic force microscopes are recognized methods for measuring or imaging surface topography. There would be a significant advantage when making microindentation hardness tests if it were possible to immediately image the results with high resolution capability. Presently known tips and control mechanisms for scanning tunneling microscopes and atomic force microscopes have heretofore prevented these instruments from being capable of both measuring surface topography and conducting microindentation hardness tests.

The tungsten scanning tunneling microscope tips generally used on these instruments are very slender and tend to bend into a fish hook shape at rather low indentation loads so that imaging after indentation is somewhat suspect. The atomic force microscope tips, although harder than the tungsten scanning tunneling microscope tips, are mounted on a delicate cantilever which is easily broken off. This limits the amount of force that can be applied with the atomic force microscope to much less than is needed for most indentations.

An alternative approach is to build a scanning tunneling or atomic force microscope with a built in scanning electron microscope which gives the imaging capability after indentation but at a considerable expense in equipment cost and added time. Also, the scanning electron microscope only works under vacuum so that observation of moist samples, such as biological specimens is not possible.

In studying mechanical properties of materials on the microscopic scale, indentation and scratch testing are two frequently used techniques. Indentation testing, where a diamond tip is forced into the material being tested is commonly used for determining hardness, and is beginning to be used to determine elastic modulus. The scratch test is used to determine (among other things) the adhesion of a film or coating deposited on a substrate. This is done by dragging the diamond tip across the sample surface under increasing load until a critical load is reached at which time some kind of delamination or failure occurs.

Normally the indentation or scratch is performed on one machine designed for that purpose, and the results are analyzed by using a microscope to determine the indent size or area of delamination. For feature sizes of a few micrometers or greater this is usually done with an optical microscope.

For features of less than a few micrometers, as are becoming increasingly important with the continued miniaturization of semiconductors and decreased thickness of protective coatings, such as used on magnetic storage disks, the area would normally be determined by scanning electron microscope imaging. This involves significant work in sample preparation, especially for samples that are electrical insulators and need to be gold or carbon coated before imaging on the scanning electron microscope. Also, just finding the tiny indent or scratch is not trivial. For the smallest indents and scratches, the atomic level resolution of the scanning tunneling microscope or atomic force microscope may be required to accurately resolve the scratch widths and areas of delamination. Researchers have reported spending up to eight hours locating an indent on the atomic force microscope after producing it on a separate microindentor.

Another source of uncertainty is plastic flow or relaxation that may take place with certain samples. If this occurs over time periods of an hour or less, an indent produced by a separate indentor may disappear before it can be inspected on a microscope. Indents made in the 50 Angstrom range, have sometimes indicated plastic deformations that could not be seen with the scanning electron microscope or atomic force microscope imaging. Possible explanations include mechanical hysterisis in the indentor causing it to indicate plastic deformation that was not actually present. It is also possible that there actually was an indent present that the researcher was not able to locate. A third possibility is that the sample exhibited a relaxation effect where the indent was actually present, but disappeared by some plastic flow phenomena before the sample could be observed in the microscope.

There would obviously be a significant advantage when making microindentation hardness and scratch tests if it were possible to immediately image the results with high resolution capability. Such capability would both reduce time and cost of the measurements and reduce uncertainties about the results.

The process of forming an indentation in a sample for micro-mechanical testing is also limited. Forces can be applied to the sample by driving the tip into the sample material using the Z-axis piezo of a scanning tunneling microscope. This process can be controlled by writing "lithography scripts" that run under the microscope control system. These scripts can be used to control the tip motion in all three axis. Simultaneous motion in Z and X or Y directions is not supported, so the force ramp desired for continuous micro-scratch testing has to be approximated using a staircase type ramp.

The magnitude of the force which can be applied is rather limited, since it is determined by the Z-axis travel of the piezo and the spring constant of the force sensor. Higher forces could be achieved by using a sensor with a higher spring constant, but that would decrease the resolution and increase the required minimum imaging force, which may cause sample wear problems during imaging. Additionally, the Z-axis travel of the piezo actuator is not compensated for linearity and hysterisis effects, as are the X and Y axis. This results in calibration problems, since there are rather large differences between the commanded Z-axis travel in the lithography script and the actual travel of the tip in the Z-axis direction.

It would be very advantageous in micro-mechanical testing to have a mechanism which provides controlled indentation of sample material at a range extending to higher maximum forces, while maintaining a high resolution and linearity between the commanded Z-axis travel and the actual travel of the tip.

Bonin et al. (U.S. Pat. No. 4,694,687) discloses a vehicle performance analyzer which incorporates a capacitive accelerometer for detecting changes in G-forces and for producing a digital count value proportional to such changes. The sensor includes a capacitive transducer comprising a pair of spaced-apart parallel plates disposed on opposite sides of a beam-supported moveable plate, which responds to changes in acceleration of forces. Bonin et al. discloses, in FIG. 3, that the beam-supported moveable plate is sealed from access between the spaced-apart parallel plates. Thus, although not physically accessible, the moveable plate will yield and be displaced when subjected to G-forces during acceleration when mounted perpendicular to such force. Bonin et al. (U.S. Pat. No. 4,694,687) is hereby incorporated by reference.

SUMMARY OF THE INVENTION

The present invention provides a force, weight or position transducer in a first embodiment. In a second embodiment, the transducer of the first embodiment is incorporated into an apparatus for microindentation hardness testing and surface imaging which allows immediate imaging of the surface subsequent to hardness testing.

First, turning to the first embodiment of the present invention, a force, weight or position transducer is provided. The output from the transducer may be converted to a DC signal proportional to the weight, force or relative position of the measured sample. This conversion may be accomplished as generally disclosed by Bonin et al. in U.S. Pat. No. 4,694,687, for example.

Additionally, the transducer may be controlled to impart a force on an object remote from the transducer or move an object remote from the transducer in a desired direction.

In one preferred embodiment, the transducer is a high precision force and displacement transducer. The transducer includes a pair of capacitive transducers. Each capacitive transducer includes a separate drive plate and a shared pick-up plate positioned between the separate drive plates. A mechanism is included for controlling the position of the pick-up plate relative to the drive plates. Additionally, a mechanism is provided for transmitting force between a remote point and the pick-up plate.

In one preferred embodiment, the position of the pick-up plate relative to the drive plate is controlled through electrostatic actuation. An electrostatic controller selectively applies a voltage to one of the drive plates providing an attractive force between the pick-up plate and drive plate. The attractive force may be transmitted by the transmitting mechanism to a point remote from the pick-up plate for movement of the remote point or applying a force to the remote point. The electrostatic controller may include a relatively high voltage power supply coupled to an amplifier.

The transducer may also include a mechanism for monitoring an output signal from the pick-up plate which is proportional to the position of the pick-up plate relative to the drive plate. In one embodiment, the monitoring mechanism includes an output signal detector/conditioner. The mechanism may include a mechanism for applying a carrier signal to the pair of drive plates. In one embodiment, the carrier signal is an AC voltage signal where the signal applied to one of the drive plates is 180 degrees out of phase with the signal applied to the other drive plate. The frequency of the carrier signal is higher relative to the frequency of the voltage applied by the electrostatic controller.

The monitoring mechanism is coupled to the pick-up plate for monitoring the transducer output signal which is representative of the displacement of the pick-up plate relative to the drive plates. The output signal may be representative of the force or movement imparted on a remote object by the transducer, or representative of a force, weight, or displacement measurement.

In another embodiment, the transducer uses a multi-capacitor system having drive and pick-up plates mounted on an appropriate suspension system to provide the desired relative motion when a force is applied to the pick-up plate or when the pick-up plate applies force or movement to an object remote from the pick-up plate. The drive plates may be driven with an AC carrier signal, in the order of 50 KHz, with the driving signals being 180 degrees out of phase with each other for providing an output signal at the pick-up plate, representative of the displacement of the pick-up plate, relative to the drive plates, and proportional to the sensed force, weight, or displacement.

The output signal is run through a buffer amplifier of very high input impedance (100 M Ohm-0.3 pF, for example), and then synchronously demodulated to produce a DC signal proportional to force or displacement. The output is positive for one direction of displacement, and negative for the opposite direction.

A sensor element in accordance with the present invention includes a pair of capacitive transducers, each transducer including a separate drive plate and a shared pick-up plate. One of the pair of drive plates may include a hole therethrough centrally disposed on the drive plate. The pickup plate is positioned between the pair of drive plates and spaced from each drive plate by an insulating spacer. Thus, the drive plates, in a preferred embodiment, generally include spaced opposing conductive surfaces when the pick-up plate is mounted therebetween. The pick-up plate can be generally a conductive central plate suspended by a spring means between the drive plates, wherein the central plate is capable of deflection between the conductive surfaces of each of the drive plates.

The sensor element includes means for transmitting force between a point remote from the central plate to the central plate. The means can include a sample holder which is attached to the pick-up plate so that it moves in unison with such plate. Alternatively, any rod or member passed through the hole in one drive plate and in contact with the central plate may transmit force to the pickup plate. The output is actually proportional to the pick-up plate position, but can easily be calibrated to represent force since the sensor may be constructed to have a linear force versus displacement relationship.

In another embodiment, the sample holder is a pedestal having a stem portion which passes through the centrally disposed hole in one drive plate and remains in contact with the surface of the conductive central plate of the pick-up plate. Contact with the central plate is approximately at its center point. Thus, the pedestal transmits a force applied to the pedestal to the central plate with resulting deflection of the central plate. A diaphragm seal can be included to prevent dust or other contaminants from entering through the space between the pedestal stem and hole in the drive plate.

In another embodiment, the transducer in accordance with the present invention includes a pair of capacitive transducers, each transducer including a separate drive plate and a shared pick-up plate. The pick-up plate is moveably mounted between the pair of drive plates. The pick-up plate may be attached directly to a remote point, without passing through one of the drive plates, for transmitting force or movement between the pick-up plate and the remote point.

The disclosed transducer is particularly useful in conjunction with scanned-probed microscopes, such as a scanning tunneling microscope or an atomic force microscope. It is, however, recognized that the transducer may be utilized in any application for measuring weight, force or displacement that requires high resolution of minute measurements. The transducer of the present invention has a resolution of over 100,000 to 1. The transducer can be of a size ½" square and ⅛" thick, which allows it to be mounted on the sample holder region of an existing scanned-probe microscope. The sample to be subjected to microscopy can then be mounted on top of the transducer. This gives a direct readout of the force applied to the sample by the microscope tip.

The signal to noise ratio of the transducers of the present invention are much higher than those calculated for existing strain gauge transducers. As previously stated, the minimum possible noise level for a strain gauge transducer is set by the thermal noise of the strain gauge element. In contrast, the capacitive transducer of the present invention has a noise level controlled by the impedance of the transducer. This allows for a signal to noise ratio of a capacitive transducer of the present invention that exceeds that of a strain gauge by more than 10 times. This can be increased even further by increasing the carrier signal beyond 50 KHz. The useable resolution is limited by thermal stability, but it is believed that the thermal stability can be improved with use of more stable materials, and that automatic correction of base line drift is also possible.

In one embodiment, the sensor element of the present invention comprises first and second, serially connected variable capacitors which may be readily fabricated using conventional printed circuit etching techniques. More specifically, the sensor comprises a stacked configuration of five substrates.

The two outermost substrates, or first and fifth substrates, have a metalized surface on each side thereof. A portion of the metal surface on the inner side of the outer most plates each comprise the first plates (drive plates) of a different variable capacitor. The first substrate further includes a hole or passage therethrough for receiving means for transmitting force to the pickup plate (from a sample holder, for example) without contacting or being frictionally restrained from movement therethrough. The pick-up plate is described more fully below. The fifth substrate further includes an area directly opposite and conforming to the size of the hole or passage in the first substrate in which the metalized surface is etched therefrom on the inner surface. This is done to maintain linearity of response of the sensor. The metalized surfaces of the outer side of the first and fifth substrates act as shields, in known manner.

The first and fifth or outer substrates each abut the second and fourth substrates, respectively, which comprise insulating substrates or frame members having an open central portion at least as large as a central plate of the third substrate described below.

The third substrate is sandwiched between these two insulating frame members. A portion of the third substrate comprises a common second plate or pick-up plate for the pair of variable capacitors defined by the first and fifth substrates. The third substrate includes a planar central plate which is suspended by spring-like members. In preferred embodiments, the spring-like members include four relatively thin L-shaped springs. The metal mass is thus displaceable within the frame openings when the five substrates are sandwiched together.

The means for transmitting force to the central plate, for example sample holder or pedestal, passes through the first and second substrate without contact, while abutting, contacting or attaching to the suspended metal mass proximate it center. In this way, forces applied to the sample holder or pedestal are translated to displacement of the suspended metal mass.

Electrical connections to various layers of substrates in the construction outlined above can be made by conductive pins inserted through metalized holes made using conventional plate through hole techniques common to multi-layered printed circuit assemblies.

Means for applying an AC carrier signal to the pair of drive plates is provided. An AC signal from a high frequency oscillator is impressed across the terminals associated with the first and fifth substrates or two outer most stationary plates of the transducer and the central displaceable plate (pick-up plate) provides an output. As such, a push-pull signal proportional to the amount of deflection of the central moveable plate is developed and subsequently amplified, and then synchronously demodulated by means for monitoring an output signal. A DC voltage signal which is proportional to force, weight or displacement can be produced.

In another embodiment, the above described sensor can also be utilized as a device for measuring ultra-microhardness of samples with the capability of simultaneous or immediately subsequent scanning tunneling microscopy or atomic force microscopy imaging. It has been found that sensors of the present invention can readily provide a full scale range of 3 grams with resolution to 30 micrograms.

When the sensor of the present invention is utilized in an apparatus for microindentation and imaging, the sensor is utilized to generate the deflection signal which is presently obtained in atomic force microscopy from the photo sensor output of a laser reflected off the cantilever. Further, with this second embodiment, the sample is mounted on the force sensor, and a suitable indentor tip or other hard, sharp tip is mounted on a scanning tunneling microscope piezo actuator. It has been found not necessary for either the indentor tip or sample to be conductive, as the force output from the sensor is sent back to the control unit, causing the system to operate much like a standard atomic force microscope.

The sample can be imaged by specifying a contact force at a suitably low value to not affect the sample. After imaging, the controller can be used together with the transducer to force the tip into the sample and produce the indent, with the transducer providing a reading of the applied load during the indenting process.

In a second embodiment, the transducer is used to force the sample into the tip to form the indent. This may be accomplished by using an electrostatic controller to apply a voltage to one of the drive plates to provide an attractive force between the pick-up plate and charged drive plate. The sample can then be reimaged with the same tip so that the results of the indent can be seen in minutes rather than hours, as would be the case When using a separate indenting apparatus.

Alternatively, the transducer pick-up plate may be connected directly or indirectly to the indentor tip. In this embodiment, the resulting movement of the pick-up plate results in the force necessary for driving the tip into the sample to perform an indentation.

Yet another embodiment of the present invention includes a high precision multi-dimensional transducer. The multi-dimensional transducer includes a first capacitive transducer for imparting force or movement and/or detecting force, weight or position in a first direction having a pick-up plate moveably mounted relative to a drive plate therein. A second capacitive transducer is included for imparting force or movement and/or detecting force, weight or position in a second direction having a pick-up plate moveably mounted relative to a drive plate therein.

The first capacitive transducer and second capacitive transducer may include means for transmitting force between an object remote from each pick-up plate and said pick-up plate. The first transducer and second transducer may further include means responsive to the position of the pick-up plate relative to the drive plate for providing an output signal proportional to said relative position.

The transducer may further include means for selectively controlling each pick-up plate. The means for selectively controlling each pickup plate may further include means for selectively imparting a force on the remote object via the pick-up plate. The means for selectively imparting a force on a remote object by the pick-up plate may include electrostatic actuation. The means for selectively controlling each pick-up plate may include a controller having an electrostatic actuator coupled to each transducer.

The multi-dimensional transducer may further include a third capacitive transducer for imparting force or movement and/or detecting force, weight or position in a third direction having a pick-up plate moveably mounted therein. Further, the multi-dimensional transducer may comprise a fourth capacitive transducer for imparting force or movement and/ or detecting force, weight or position in the second direction having a pick-up plate moveably mounted therein.

The multi-dimensional capacitive transducer has many applications, including use in a micro-mechanical test system. In one preferred embodiment, the present invention includes a scanned probe microscope apparatus, including a high precision, multi-dimensional capacitive transducer in accordance with the present invention. The multi-dimensional transducer, in accordance with the present invention, may be used to provide in situ imaging in micro-mechanical test systems.

The present invention further includes a method of performing a micro-mechanical test on a sample. The method includes the steps of placing the sample. The micro-mechanical test is performed using a high-precision, multi-dimensional capacitive transducer.

The method may further include the step of the imaging the sample in place using the multi-dimensional capacitive transducer. The step of performing the micro-mechanical test using the multi-dimensional capacitive transducer may further include imparting force or movement and/or detecting force, weight, or position in a first direction; and imparting force or movement and/or detecting force, weight, or position in a second direction. The step of performing the micro-mechanical test may further include the step of imparting force or movement and/or detecting force, weight, or position in a third direction.

These and various other advantages and features of novelty which characterize the present invention are pointed out with particularity in the claims annexed hereto and forming a part hereof. However, for a better understanding of the invention, its advantages, and the object obtained by its use, reference should be made to the drawing which forms a further part hereof, and to the accompanying descriptive matter in which there are illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views:

FIG. 3 is a schematic representation of another embodiment incorporating the transducer of the present invention as both a force or movement imparting device and as a force, weight, or displacement measuring device;

FIG. 3A is an equivalent circuit diagram of the measuring device shown in FIG. 3, incorporating the transducer of the present invention;

FIG. 9 is a top view of one structural embodiment of the multi-dimensional capacitive transducer shown in FIG. 8;

FIG. 10 is a side view of the structural embodiment of the multi-dimensional transducer shown in FIG. 9;

FIG. 11C is another schematic representation incorporating the multi-dimensional transducer of the present invention as a force or movement imparting device and/or a force, weight or displacement measuring device;

FIG. 11D is one structural embodiment of the multi-dimensional transducer in accordance with the present invention shown in FIG. 11C;

DETAILED DESCRIPTION OF THE PREFERRED EMBODIMENTS

Detailed embodiments of the present invention are described herein. However, it is to be understood that the disclosed embodiments are merely exemplary of the present invention which may be embodied in various systems. Therefore, specific details disclosed herein are not to be interpreted as limiting, but rather as a basis for the claims and as a representative basis for teaching one of skill in the art to variously practice the invention.

The present invention includes generally two embodiments. The first embodiment directed to a transducer capable of imparting a force on or moving an object remote from the transducer, which may also be used as a force or position indicating device or transducer, and the second embodiment directed to an apparatus for microindentation hardness testing and subsequent surface imaging of the results with high resolution capacity. The second embodiment utilizes, in preferred designs, the transducer element of the first embodiment. The force or position imparting/indicating device or transducer is thus described first. The apparatus for micro-hardness testing and subsequent surface imaging utilizing the transducer is then described, recognizing that the disclosure with regard to the transducer alone is equally applicable to the test apparatus utilizing such transducer.

The force (including weight) or position indicating device or transducer of the present invention generally has three components. The first component is a transducer, which includes a multi-plate capacitor system. The second component is means for controlling the transducer for imparting a force on or moving an object remote from the transducer. The third component includes means for applying an AC carrier signal, and means for monitoring the transducer output, which may include an output signal detector/conditioner, preferably converting the output from the transducer to a DC signal proportional to force, weight or displacement.

Figure 1:
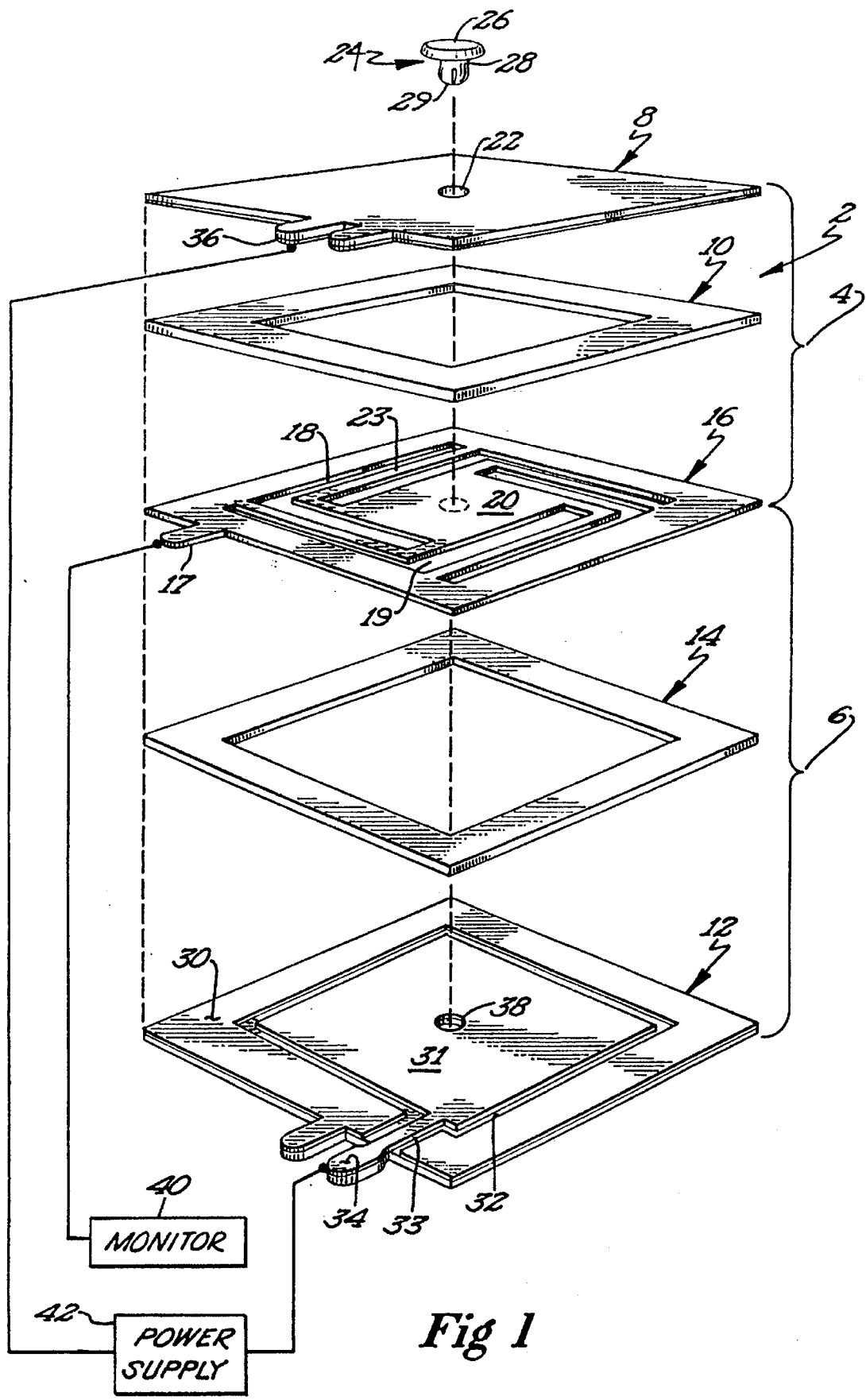
FIG. 1 depicts an exploded view of a capacitative transducer in accordance with the present invention.

Referring now to FIG. 1, an exploded view of the components of the sensor element 2 of the present invention, is depicted. Functionally, the sensor element comprises two transducers 4, 6, which function as two variable capacitors connected in series and forming a capacitive voltage divider. The overall sensor element 2 includes five substrate layers 8, 10, 16, 14, 12 sandwiched together to form the transducers. The sensor element 2 can be fabricated using well-known printed circuit etching technology.

The first substrate layer 8 and the fifth substrate layer 12 include the drive plates or fixed plates of the transducers and are driven with a carrier signal. The carrier signal can be an AC signal on the order of 50 KHz, with the signal to these outer most substrate layers 8, 12, being 180 degrees out of phase with each other.

The outer exposed surfaces of first substrate 8 and fifth substrate 12 are covered with metalization, for example, copper. This metal layer functions as a shield against EMI noise. On the inner surface of first substrate 8 and fifth substrate 12, a metalized pattern 30 is provided. This metalized pattern forms the drive plate on each substrate. The metalized pattern on the interior surface of the first substrate 8 generally corresponds to that on the fifth substrate 12. As depicted in FIG. 1, the metalized pattern 30 or drive plate on the inside of the fifth substrate 12 can include a generally rectangular frame pattern 31. Extending around the periphery of the substrate metalized pattern 31 is a channel defining an unmetalized opening 32. Centrally disposed in this unmetalized opening 32 is the rectangular metalized pattern 31 of conductive material, having a conductive lead 33 leading to a conductive terminal portion 34.

The metalization on the inside surface of the first substrate 8 is similar to that of the inside surface of fifth substrate 12 with two exceptions. The first difference is that the terminal portions of each substrate 34, 36 are offset from one another, rather than being vertically aligned when the sensor element 2 is assembled. The second difference is the provision of a through hole 22 centrally disposed through the thickness of the first substrate 8. The through hole 22 is disposed centrally for receiving a sample holder 24 or other means for transmitting force therethrough, which is described in further detail below.

The inside surface of the fifth substrate 12 includes a demetalized or etched portion 38 which corresponds to the through hole 22. The provision of the demetalized or etched portion 38 generally corresponding to the through hole 22 provides for the rectangular metalized pattern 30 of conductive material on each of the first substrate 8 and fifth substrate 12 inside layers to be mirror images of one another. This provision is necessary to provide a linear response from the pair of capacitive transducers 4, 6.

The outer layers of the sensor element 2 or first substrate 8 and fifth substrate 12 can be manufactured from standard circuit board materials, such as 1/16" glass epoxy with copper on both sides. In order to reduce labor requirements, a large number of the outer layer substrates may be manufactured at one time. For example, a 6" sheet of material may be utilized to manufacture about 100 substrate layers of 1/2" square dimensions. The pattern for the metalized portion 30 of the first substrate 8 and fifth substrate 12 may be first etched in the copper. The substrate may be routed around the individual devices within a large sheet of material, leaving only thin tabs of materials to hold them together. These tabs allow the devices to be snapped apart after assembly.

The second substrate layer 10 and the fourth substrate layer 14 comprise spacer layers. As depicted in the figure, these layers 10, 14 may be of generally rectangular shape and have a generally rectangular opening formed with the therein, with the opening extending completely through the substrate. The spacer layers, second substrate 10 and fourth substrate 14, must be insulators or covered with an insulating coating. The opening through the insulators 10, 14 is equal to or greater than the dimensions of a central plate 20 on a third substrate 16 described below, and an associated appropriate suspension system 18, also described below.

The second substrate 10 and fourth substrate 14 can be manufactured from etched metal with an insulating coating on both sides. This insulating coating could be an epoxy, or other organic coating such as those used on enameled magnet wire, but it is believed that best results are achieved by using aluminum for the spacer and anodizing it to form an insulating coating of aluminum oxide.

It is believed that the insulating spacers, second substrate layer 10 and fourth substrate layer 14, can be etched first and then anodized, or anodized first and then etched, depending upon the type of photoresist chemicals used. A preferred method is to use aluminum sheet stock purchased with a thin (0.00012") anodized layer on both sides. This anodized layer provides good adhesion with the positive type liquid photoresist which can be used to fabricate the other layers of the sensor element 2. With bare aluminum, the resist tends to peel away at the edges being etched making it hard to maintain desired dimensions.

After etching, the photoresist and original anodizing are removed and the parts are anodized to the desired insulation thickness. Although it is believed 0.0005" or less of an anodized thickness layer will provide the required electrical isolation, it is desirable to make the thickness as great as possible to minimize the capacitance between the outer layer shields, first substrate layer 8 and fifth substrate layer 12, and a center plate, third substrate layer 16, described below.

The third substrate layer 16 is sandwiched between the insulating layers, second substrate layer 10 and fourth substrate layer 14. The third substrate layer 16 includes the pick-up plate which is common to the pair of transducers 4, 6. A central plate 20 is mounted on an appropriate suspension system 18 to provide for desired relative motion of the central plate 20 or pick-up plate on third substrate layer 16. The third or central substrate layer 16 can be an etched metal layer supported by a suspension system 18 defined by a pattern of slits 19. The central plate 20 is thus a solid portion or mass suspended by the surrounding framework of a suspension system 18. The third substrate layer further includes a terminal 17 for electrical connection. A preferred metal for use as a central plate is a beryllium-copper alloy.

Although a pattern of four L-shaped slits 19 are depicted in the figure, it is believed that other patterns may be utilized to provide the same type of spring supporting structure for central plate 20. Further, it is recognized that varying effective spring constants may be achieved for the centrally supported mass or central plate 20 by altering the thickness of the materials of this substrate and the size of the spring elements. Thus, the overall range of travel per unit force exerted on the central plate 20 of the third substrate layer 16 may be varied by design. Thus, sensors of varying overall range may be manufactured.

When the five substrate layers 8, 10, 16, 14 and 12 are assembled together, the central plate 20 of the third substrate layer 16 is centrally disposed within the openings formed in the insulating substrates, second substrate layer 10 and fourth substrate layer 14, and thus, the central plate 20 is free to deflect relative to the first substrate layer 8 and fifth substrate layer 12.

The layers may be assembled together by hand, holding them together with pins inserted around the entire perimeter of the substrates and soldered to the outside layers. When assembled, selected electrical connections between the various internal layers or substrates can readily be provided as disclosed by Bonin et al. in U.S. Pat. No. 4,694,687.

Means for transmitting force 24 between a point remote from the central plate 20 and the central plate 20 are provided. This means can include a sample holder 24, which functions to transmit the force created by the weight of a sample to the central plate 20 of the third substrate layer 16;

and for transmitting force and movement from the central plate 20 to the sample holder 24 (or other device) for performing indentations or other micromachining operations. The means for transmitting force and movement from the central plate 20 to an object remote from central plate 20, such as sample holder 24 or through connection of central plate 20 to the remote object, is described in detail later in this application.

In a preferred embodiment, the sample holder 24 is a pedestal which includes a sample holding surface 26 and a stem portion 28. The stem portion 28 extends through the through hole 22 in the first substrate layer 8 and through the opening in the second substrate layer 10. The bottom surface 29 of the stem portion 28 contacts the upper surface of the central plate 20 at a central point 23 when the sensor is assembled. The space between the stem portion 28 and wall of the through hole 22 is preferably sealed from contamination by a diaphragm seal or other sealing means which prevents entry of dirt while not impeding movement of the pedestal or other means for transmitting force 24.

Thus, functionally, the weight or force exerted by a sample or other means on the sample holding surface 26 of the sample holder 24 is transmitted to the central plate 20 of the third substrate layer 16 and results in deflection of the central plate 20 commensurate with the force exerted on the surface of the sample holder 24. Thus, the central plate 20, under force, moves closer toward or further away from one or the other of the outer most substrates, first substrate layer 8 and fifth substrate layer 12. Of course, the sample holder 24 may be directly connected to a moving, or force imparting, element without positioning a "load" on the surface 26. Indeed, the surface 26 may be replaced by a connector adapted for this purpose.

Means for providing a carrier signal 40 to the outer most plates or first substrate layer 8 and fifth substrate layer 12 are provided. This signal can be an AC signal. Such means may include an oscillator which produces a 50 KHz alternating current signal. The signal to each outer most plate is preferably 180 degrees out of phase with the signal provided to the other outer most plate.

Means are also provided for reading the output 42 from the sensor element 2, and converting the output to a signal proportional to force, weight or displacement of the central plate 20. The output signal is generally run through a buffer amplifier of very high input impedance (100 MOHM-0.3 pF), and then synchronously demodulated to produce a DC signal. The DC signal is proportional to the force, weight or displacement of the central plate 20. The output would be positive for one direction of displacement, and negative for the opposite direction. It is recognized that the sample holder 24 or means for transmitting force is attached or in contact with the central plate 20 to move in unison with such central plate 20. The output of the sensor 2 is actually proportional to the central plate 20 position, but can easily be calibrated to represent force (including weight) since the sensor has a linear force versus displacement relationship.

It is recognized that the sample holder 24 or means for transmitting force must be manufactured from an insulating material or covered with an insulating material. Further, the clearance between the inside diameter of through hole 22 and the outside diameter of stem portion 28 must be sufficient to avoid any frictional effects which may reduce the sensitivity of the sensor element 2.

The signal to noise ratio of the capacitive transducers of the present invention are much better than that of presently used metal strain gauge transducers. The minimum noise level of the strain gauge transducer is determined by the thermal noise of the strain gauge resistive element. This noise is proportional to the square root of the resistance. The output signal is proportional to the input signal, but is only a very small fraction of it. A typical value taken from a commercial scale strain gauge transducer is 175 Ohm resistance at full scale output of 5 millivolts.

The three-plate capacitive transducer of the present invention does not generate noise as a resistive transducer does, but the signal cannot be used without connecting it to an amplifier, and the amplifier must have a very high input resistance, so the amplifier will generate noise. The lower limit of this noise will be determined by the effective input impedance of the amplifier. Since the capacitive transducer is in parallel with the amplifier input impedance, and the amplifier input impedance is much larger than the impedance of the transducer (or the output will be very non-linear), the effective input impedance is equal to that of the transducer.

The impedance of the transducer is determined by the capacitance and operating frequency. Higher operating frequency gives lower transducer impedance ($X_c=1/6.28FC$). The capacitance is about 10 pF for the ½" square device with 0.005" spacing between plates. The operating frequency can be any convenient value, limited only by the frequency response of the amplifier and associated circuitry. The full scale output signal of the transducer is equal to the input voltage, which will be conservatively taken as 10 volts. The full scale output of the capacitive transducer is 10 V, which is 2,000 times greater than the strain gauge transducer (5 mV). The impedance, and therefore the noise generated, is greater with the capacitive transducer (except at very high frequencies which would require rather expensive components), but due to the much higher inherent output level, the signal to noise ratio of the capacitive transducer is significantly better.

The following table shows the relationship of signal to noise ratio for the two transducers.

TABLE 1

Fop = operating frequency of capacitive transducer
C = capacitance of transducer = 10 pF
Xc = impedance of transducer = $1/(6.28 \times Fop \times C)$
R = resistance of strain gauge = 175 Ohm
Since noise is proportional to the square root of R or Xc, the ratio of capacitive transducer noise to strain gauge noise is the square root of (Xc/R), and the factor of improvement of SNR of capacitive vs strain gauge is 2000 divided by the square root of (Xc/R).

| Fop | Xc/R | square root Xc/R | 2000/sq root (Xc/R) |
|---|---|---|---|
| 10 KHz | 11,400 | 107 | 19 |
| 100 KHz | 1,140 | 34 | 59 |
| 1 MHz | 114 | 11 | 190 |
| 10 MHz | 11.4 | 3.4 | 590 |
| 100 MHz | 1.14 | 1.1 | 1900 |

Capacitive transducer SNR is better than strain gauge by factor in above column.

As is readily apparent from the above table, the capacitive transducer of the present invention is far superior to strain gauges on the basis of electronic noise.

Since the output of the capacitive transducer or sensor element 2 is proportional to the displacement of the center mass portion 20 or electrode, it is recognized that a device for use as a scale or as a measure of displacement may be manufactured. It is first necessary to choose an appropriate stiffness for the suspension system 18 supporting the central plate 20 so that the sample holder 24 or means for transmitting force is forced reliably against the surface to be measured without exerting excessive force that would deflect the object and change its actual position. Secondly, it is recognized that the insulating spacers, second substrate layer 10 and fourth substrate layer 14, may be manufactured of different thicknesses to offset the center plate sufficiently. This would alter the operational range of the device. Experimental results to date have given resolutions of better than 10 Angstroms.

Figure 2:
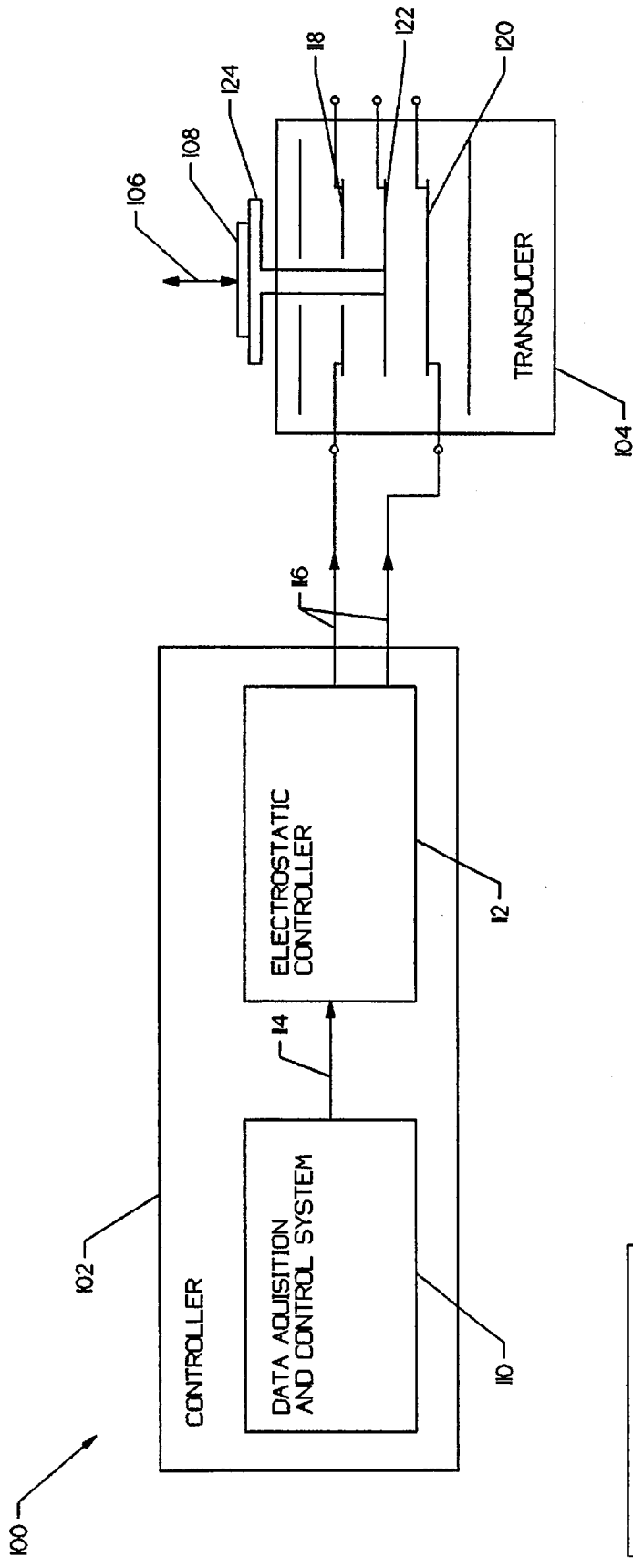
FIG. 2 is a schematic representation incorporating the transducer of the present invention as a force/movement imparting device.

Referring to FIG. 2, the transducer of the present invention is shown generally at 100 as a force or movement imparting system. In system 100, controller 102 is coupled to a transducer 104. Transducer 104 can be similar to the multiplate capacitor transducer system shown in FIG. 1. Transducer 104 is responsive to controller 102 for selectively providing a force or movement output to a point remote from transducer 104, indicated at 106.

In one preferred embodiment of the system 100, shown in FIG. 2, the system 100 includes controller 102 having a data acquisition and control system 110 electrically coupled to an electrostatic controller 112, indicated at 114. Electrostatic controller 112 is electrically coupled to transducer 104, indicated at 116.

Similar to the multi-plate capacitive transducer shown in FIG. 1, transducer 104 includes a multi-plate capacitor having a drive plate 118, a drive plate 120, and a pick-up plate 122. Mechanically coupled to pick-up plate 122 is transmitting means 124. Transmitting means 124 transmits force or movement between center plate 122 and remote object 108.

In operation, electrostatic controller 112 applies a relatively high voltage to drive plate 118 and/or drive plate 120 of transducer 104. Drive plates 118 and 120 are fixably mounted within transducer 104, and pick-up plate 122 is movably mounted within transducer 104. In a preferred embodiment, electrostatic controller 112 applies a relatively high voltage to drive plate 118. The electrostatic attraction between the movably mounted pick-up plate 122 and the fixed drive plate 118 pulls the pick-up plate 122 closer to drive plate 118. When pick-up plate 122 is moved closer to drive plate 118, force transmitting mechanism 124 transmits the corresponding force or movement to remote object 108.

Electrostatic controller 112 may be manually or automatically controlled through data acquisition and control system 110. In one preferred embodiment, electrostatic controller 112 includes a DC power supply coupled to an amplifier for applying a DC voltage to drive plate 118. The voltage applied to drive plate 118 may be selectively varied by data acquisition and control system 110. As the voltage applied by the electrostatic controller 112 to the drive plate 118 is increased, the electrostatic attraction between pick-up plate 122 and drive plate 118 increases, and pick-up plate 122 is pulled closer to drive plate 118.

In one embodiment, electrostatic controller 112 includes a DC power supply coupled to an amplifier for applying a maximum DC voltage to pick-up plate 118 of 600 volts. In this embodiment, the maximum force transmitted through force transmitting mechanism 124 to remote object 108 is about 10 mN. Although a maximum force of 10 mN is adequate for most practical test instruments, it is recognized that it is possible to significantly increase the force. In one embodiment, the force is increased by reducing the spacing between drive plate 118 and pick-up plate 122, and using different thickness spacers in the transducer 104 assembly.

It is recognized that electrostatic controller 112 may be coupled to either drive plate 118 or drive plate 120 for imparting a force or movement of an object remote from pick-up plate 122. Alternatively, as shown in FIG. 2, electrostatic controller 112 may be coupled to both drive plate 118 and drive plate 120 for applying a relatively high voltage to drive plate 118 and drive plate 120 for using transducer as a force imparting and/or as a positioning device. Additionally, a single capacitor system may be utilized, where electrostatic controller 112 is coupled to the single drive plate 118. Similar to a multiple capacitor system, when electrostatic controller 112 applies a voltage to drive plate 118, pick-up plate 122 is attracted to drive plate 118 resulting in force transmitting mechanism 124 transmitting a corresponding force or movement to remote object 108.

Additionally, FIG. 2 shows force transmitting mechanism 124 extending from pick-up plate 122 through a hole centrally disposed in drive plate 118 to remote object 108 for transmitting forces and movement between pick-up plate 122 and remote object 108. It is recognized that transducer 104 may take on many different shapes and forms while still remaining within the scope of the present invention. Force transmitting mechanism 124 may transmit force or movement from pick-up plate 122 to remote object 108 without passing through drive plate 118, or remote object 108 may be in direct contact with pick-up plate 122 for imparting forces and movement between pick-up plate 122 and remote object 108.

Figure 2A:
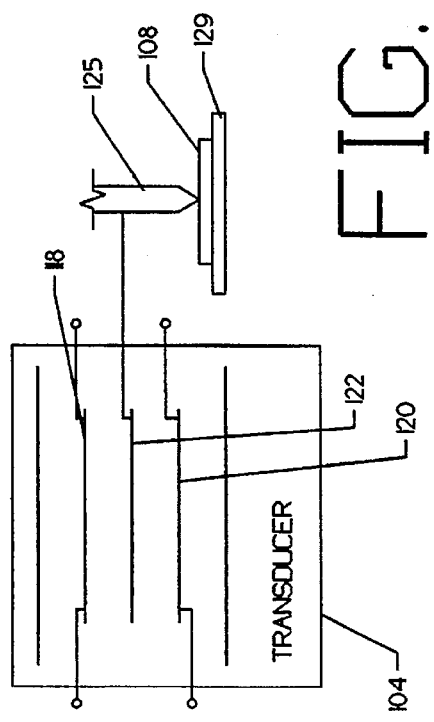
FIG. 2A is a schematic representation of another embodiment of the transducer shown in FIG. 2.

In another embodiment of the present invention shown in FIG. 2A, pick-up plate 122 may be directly or indirectly connected to remote object 108, without passing through drive plate 118 or drive plate 120. In this embodiment, pick-up plate 122 may impart forces or movement between pick-up plate 122 and remote object 108. In one embodiment shown in FIG. 2A, pick-up plate 122 may impart forces on a remote object 108 having a tip 125, for performing indentation of a sample 108 located on a sample holder 127.

The force generated by electrostatic actuation can be calculated as:

$$F=KV^2$$

where force is in Newtons, K is the force constant in Newtons/volt squared, and V equals volts. The exact value of force constant K may vary with the weight of remote object 108, since this changes the internal spacing between plates 118, 122 and 120 in transducer 104. In the embodiment shown in FIG. 2, the force constant K may be determined using a simple lab test, such as measuring the transducer force versus electrostatic potential at a constant position by adding test weights and determining the voltage required to balance the force of those weights. With this method, the pick-up plate 122 is always at the same position, so the electric field is proportional to the applied voltage.

It is also recognized that changes may be made in the multi-plate capacitive transducer 104 to change or improve the performance of the system, while still remaining within the scope of the present invention. For example, non-conducting spacers may be located between drive plate 118 and drive plate 120, and pick-up plate 122, or alternatively, the transducer 104 could be filled with a dielectric fluid to prevent phenomena such as corona breakdown. If corona discharge is present, ionized air inside the transducer 104 could vary the relative capacitance between the drive plates 118 and 120, and pick-up plate 122, and could result in an erroneous output for transducer 104.

FIG. 3 shows another embodiment of the present invention. In addition to the system 100 shown in FIG. 2, oscillator 130 is included for applying a carrier signal to the multi-plate capacitor system of transducer 104 for measuring the displacement of pick-up plate 122 relative to drive plates 118 and 120, which is proportional to force, weight or position. In one preferred embodiment, oscillator 130 is electrically coupled to drive plate 118 and drive plate 120. Oscillator 130 produces an AC carrier or high frequency signal which is applied to each drive plate 180 degrees out of phase with the signal provided to the other drive plate. In general, the carrier frequency applied to each drive plate is higher than the frequency of the electrostatic control signal so interference between the two signals may be eliminated.

Additionally, buffers B1 and B2 are located between electrostatic controller 112 and transducer 104, and oscillator 130 and transducer 104, respectively, for isolation. With buffers B1 and B2, oscillator 130 is not affected by the high voltage supply of electrostatic controller 112 and electrostatic controller 112 is not affected by the oscillator 130 signal. In one preferred embodiment, buffer B1 is a pair of 1 megohm resistors and buffer B2 includes a pair of 1,000 picofarad capacitors.

Output signal detector/conditioner 132 is coupled to pick-up plate 122 for reading the transducer 104 output signal, indicated at 131, resulting from oscillator 130 applying the carrier signal to the drive plates 118 and 120. The output signal 131 of transducer 104 is proportional to the pick-up plate 122 position, which is representative of the sensed force, weight, or displacement.

Output signal detector/conditioner 132 converts the output signal 131 from pick-up plate 122 to a signal proportional to force, weight or displacement with respect to the pick-up plate 122. In one embodiment, the output signal is run through a buffer amplifier of very high input impedance (100 Megohm-0.3pF) and then synchronously demodulated to produce a DC signal. The DC signal is proportional to force, weight or displacement of the pick-up plate 122. Additionally, an input signal 133 may be provided to data acquisition and control system 110 from output signal detector/conditioner 132 when using controller 102 to control the position of pick-up plate 122 relative to drive plate 118 and drive plate 120.

FIG. 3A is an equivalent circuit diagram of the measurement system shown in FIG. 3, which includes oscillator 130 and multi-plate capacitive transducer 104. Nodes 1, 2, and 3 of FIG. 3A correspond to nodes 1, 2, and 3 of transducer 104 shown in FIG. 3. As shown, transducer 104 is modeled as a capacitive voltage divider with oscillator 130 providing an input AC carrier signal 180 degrees out of phase at each node 1 and 2, with a voltage output signal at node 3. The voltage output signal at node 3 is determined by the ratio of the capacitance between nodes 1 and 3, and the capacitance between nodes 2 and 3.

As previously detailed, by oscillator 130 providing a carrier signal to drive plates 118 and 120 of transducer 104, output signal detector/conditioner 132 monitors the output signal at pick-up plate 122 which is proportional to the position of pick-up plate 122 relative to drive plates 118 and 120. Therefore, when electrostatic controller 112 applies a voltage to drive plate 118 to attract pick-up plate 122 towards drive plate 118 for imparting a force on remote object 108, the force imparted on remote object 108 may be determined by the ratio of the square of the applied voltage multiplied by the force constant, as previously explained. The output signal on pick-up plates 122 is directly proportional to the position of pick-up plate 122.

Figure 4:
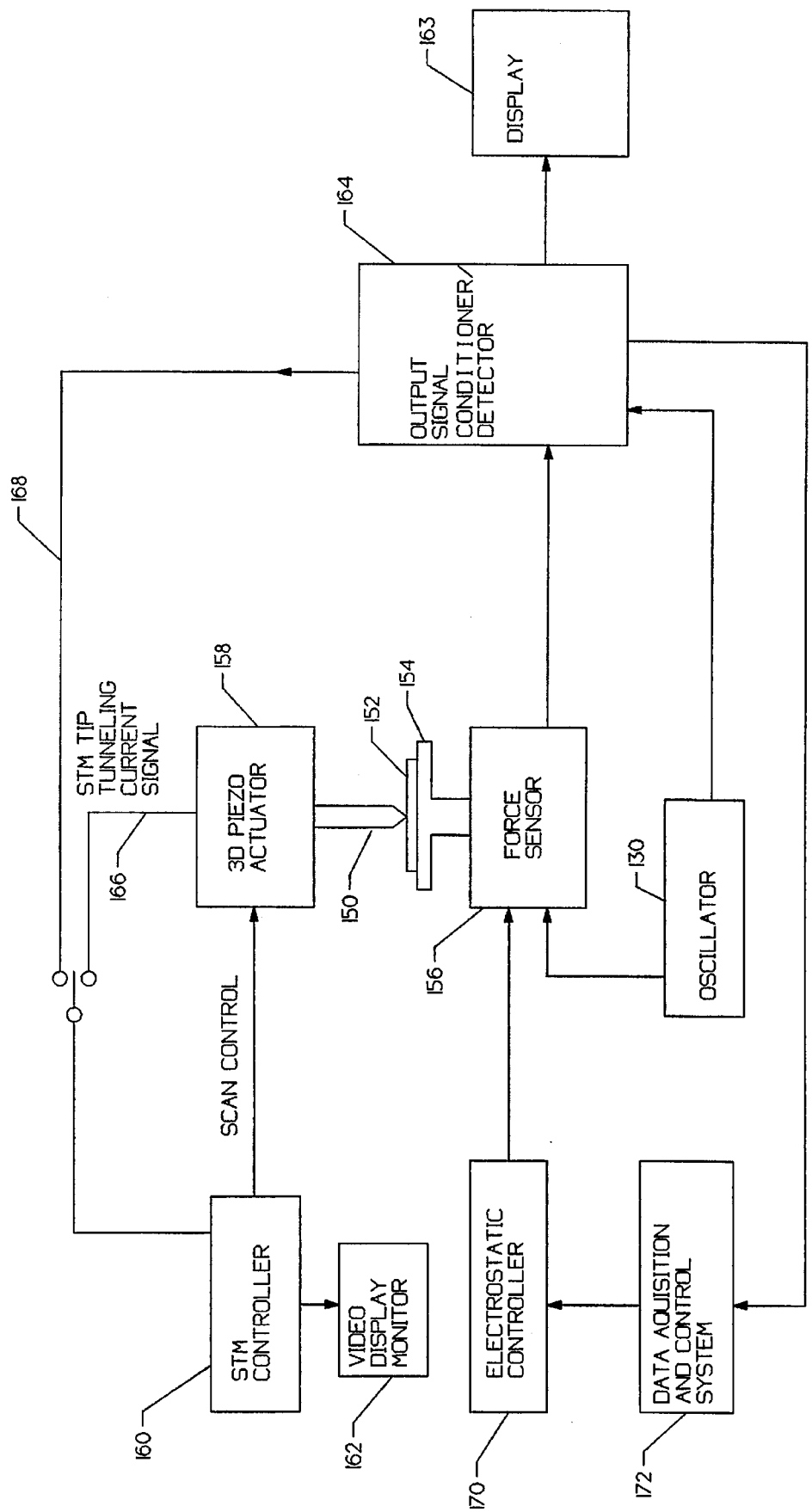
FIG. 4 is a schematic representation of an apparatus for hardness testing and surface imaging incorporating the transducer of the present invention.

Now referring to FIG. 4, a schematic representation of an apparatus for hardness testing and surface imaging incorporating the above-described transducer of the present invention is depicted. With this embodiment, it is possible to conduct a scan of the surface topography of a sample, followed immediately by microindentation testing, followed by a second imaging of the surface topography all on the same instrument. Generally, the schematic in FIG. 4 depicts a commercial scanning tunneling microscope, such as the Nanoscope III, available from Digital Instruments, which has been modified to conduct the in-situ high resolution imaging and microindentation testing on a single instrument.

As previously stated, scanning tunneling microscopes are commercially known. As disclosed by Wickramasinghe in "Scan-Probe Microscopes", *Scientific American*, October, 1989, pp. 98–105, which is incorporated herein by reference, scanning tunneling microscopes include several standard components which are depicted in FIG. 4.

With a scanning tunneling microscope, a sample 152 is placed on a sample platform 154 for analysis. The scanning tunneling microscope senses atomic-scale topography by means of electrons that tunnel across the gap between a probe 150 and the surface of the sample 152. A scanning head 158 has the probe mounted thereon. The scanning head 158 (in the illustrated embodiment, a 3-D piezo actuated head) is utilized to move the probe in three directions in response to changes in applied voltage. Piezo electric ceramics are generally utilized because they change size slightly in response to such changes in voltage, and thus, maneuver the probe in three dimensions. The voltage applied to the scanning head 158 is controlled by the scanning tunneling microscope controller 160.

In use, voltage is applied to the tip of the probe 150 and it is moved toward the surface of the sample 152, which must be conducting or semiconducting, until a tunneling current starts to flow. The tip of the probe 150 is then scanned back and forth in a raster pattern by varying the voltage to the piezo electric ceramics which control horizontal motion. The tunneling current tends to vary with the topography of the sample, and therefore, a current output signal 166, which provides a feedback mechanism, and which monitors such tunneling current, feeds such signal to the scanning tunneling microscope controller 160. The controller 160 adjusts the output to the scanning head 158 which responds by moving the tip of the probe 150 up and down, following the surface relief. The probe 150's movements are translated into an image of the surface and displayed on an image display 162.

With scanning tunneling microscopy, the probe 150 is generally made from tungsten with a tip so fine that it may consist of only a single atom and measures as little as 0.2 nanometers in width.

The apparatus of Applicant's present invention for microindentation with subsequent surface imaging utilizes the above-described scanning tunneling microscope with several modifications. A transducer 156, as described in the first embodiment, is mounted on the scanning tunneling microscope base in place of the standard sample holder. The sample 152 is then mounted on the sample platform 154. An output signal conditioner/detector 164 is operatively connected to the transducer 156 to monitor the output signal from the transducer 156 and convert it to a signal proportional to the force being applied to the sample 152 on the platform 154 by the probe 150. The output signal conditioner/detector or transducer output signal may then be utilized to control the vertical position of the probe 150 or position along the Z axis by sending such signal through the scanning tunneling microscope controller 160 during surface imaging. Alternatively, the output from the output signal conditioner/detector 164 can be monitored for measurement of force being applied during microindentation or micro hardness testing. The monitored output from output signal conditioner/detector may be displayed on display 163. These procedures are described below.

The scanning tunneling microscope described above is also modified by replacing the tungsten probe with a harder tip for microindentation testing. In a preferred embodiment, a diamond tip is used, such as blue diamond. It is not necessary for the tip to be conductive or a sample being tested to be conductive; however, it is recognized that conductive blue diamond scanning tunneling microscope tips are available. They can be used for scanning tunneling microscopy imaging of conductive samples, as well as testing with Applicant's apparatus.

In operation, the transducer 156 of Applicant's second embodiment is used for applying the force during indentation or scratching, measuring the applied force during indentation or scratching, and for imaging before and after testing. An atomic force microscope type image is first obtained from the scanning tunneling microscope by disconnecting the scanning tunneling microscope's tunneling current output signal 166 and substituting in its place the output signal 168 from the output signal conditioner/detector 164. The scanning tunneling microscopes scanning function can then be operated in a normal manner, with the output signal conditioner/detector 164 output signal now controlling the Z axis piezo ceramic to maintain a constant force between the probe 150 tip and the sample 152, rather than a constant tunneling current. Alternatively, a constant height image could be obtained where the probe 150 tip Z-position or vertical height is held constant, and the image is obtained directly from the transducer 156 output signal from the output signal conditioner/detector 164, which again passes through the scanning tunneling microscope controller 160 and results in a display of surface topography on the image display 162.

Once an image of the surface has been made using the above procedure, the controller can be used to force the tip into the sample and produce an indent, with the force sensor providing a reading of the applied load during the indenting process. Additionally, the transducer 156 can be used to force the sample into the tip to form the indent. In particular, in a preferred embodiment, an electrostatic controller 170 can be manipulated to selectively apply a voltage to transducer 156, allowing transducer 156 to provide force to force the sample into the tip 150, which provides an indentation. Alternatively, transducer 156 may be connected to tip 150 for forcing the tip into the sample for indentation.

The force provided by transducer 156 for indentation may be selectively controlled by manual operation of electrostatic controller 170, or through automatic operation of electrostatic controller 170 by data acquisition and control system 172. Data acquisition and control system 172 may include a microprocessor or similar logic based system for calculating the voltage to apply to generate a desired force from transducer 156. Additionally, output signal conditioner/detector 164 is electrically coupled to data acquisition and control system 172. Data acquisition and control system 172 may be used to adjust the force applied by transducer 156 to compensate for movement of the sample as indentation occurs, which is known to occur in softer samples. The force provided by transducer 156 may also be changed by output signal conditioner/detector 164 based on the output signal received from transducer 156.

After indentation, the sample can then be reimaged with the same tip so that the result of the indent can be seen in minutes, rather than hours, without the need for moving the sample or finding the point where the indentation was made in the sample. Further, because the first image, indentation, and second image are all made with the sample in a single position, it is assured that the first surface image and second surface image are of the same surface area and show the corresponding effect of the indentation step.

With the above-described system, both conducting and nonconducting samples can be imaged at high resolution before and after mechanical testing without disturbing the sample position so that there is no problem of trying to locate the test region as there is when using separate indenting and imaging equipment. It is also possible to compare side by side atomic force microscope images and scanning tunneling microscope images of the same sample surface by flipping a switch to change from atomic force microscope to scanning tunneling microscope. This is sometimes useful as the atomic force microscope signal is generally an accurate representation of the sample topography, while the scanning tunneling microscope signal may give some information about conductivity or electronic states of the surface.

The apparatus for microindentation hardness testing and/or surface imaging of the present invention has been described with respect to a preferred embodiment in which a scanning tunneling microscope apparatus is utilized having a base for mounting a sample thereon and a piezo actuated head having a probe mounted thereon for operative engagement of a sample mounted on the base for measuring surface typography. In this embodiment, a probe is mounted on the piezo actuated head, while the transducer is mounted on the base for mounting a sample thereon. With this arrangement, the scanning head or piezo actuated head moves the probe in a raster pattern over the surface dimension typography. It is, however, recognized that other arrangements of the probe, transducer and scanning head are possible within the scope of the present invention. The key to operation of applicant's invention is that a scanned probe microscope apparatus incorporates a probe in a scanning head arranged for operative engagement of a surface of a sample for measuring a surface typography thereof. The probe has a hardness greater than a sample to be tested and the transducer is operatively located to measure the force between the sample and the probe when operatively engaged in the surface thereof and for imparting a force and measurement displacement for performing indentations or other micromechanical tests.

As previously stated, in a first preferred embodiment, scanned probe microscope includes a base for mounting a sample thereon and a piezo actuated head having a probe mounted thereon, with the transducer mounted on the base and the sample resting thereon. In a second preferred embodiment, the transducer may be mounted on a fixed surface with the probe affixed to the transducer. The sample may be mounted on a sample holder which incorporates a piezo actuated head or scanning head. With this arrangement, the piezo actuated scanning head moves the sample against the probe with the force applied to the probe translated through the transducer to measure the force.

In a third alternative embodiment, the sample having a surface to be scanned may be a large sample on which an instrument of the present invention may be mounted. The instrument would include the probe mounted on the transducer, which in turn is mounted on the piezo actuated or scanning head. With this arrangement, the probe is placed to engage the surface of the large sample and the transducer is again utilized to measure the force of contact, while the scanning head moves the probe over the surface for imaging.

In a fourth alternative embodiment, the probe can be mounted on a fixed surface. With this arrangement, the sample and transducer are mounted on the piezo actuated or scanning head. Thus, the scanning head moves the sample over the fixed probe with the transducer measuring the force between such probe and sample.

Figure 5:
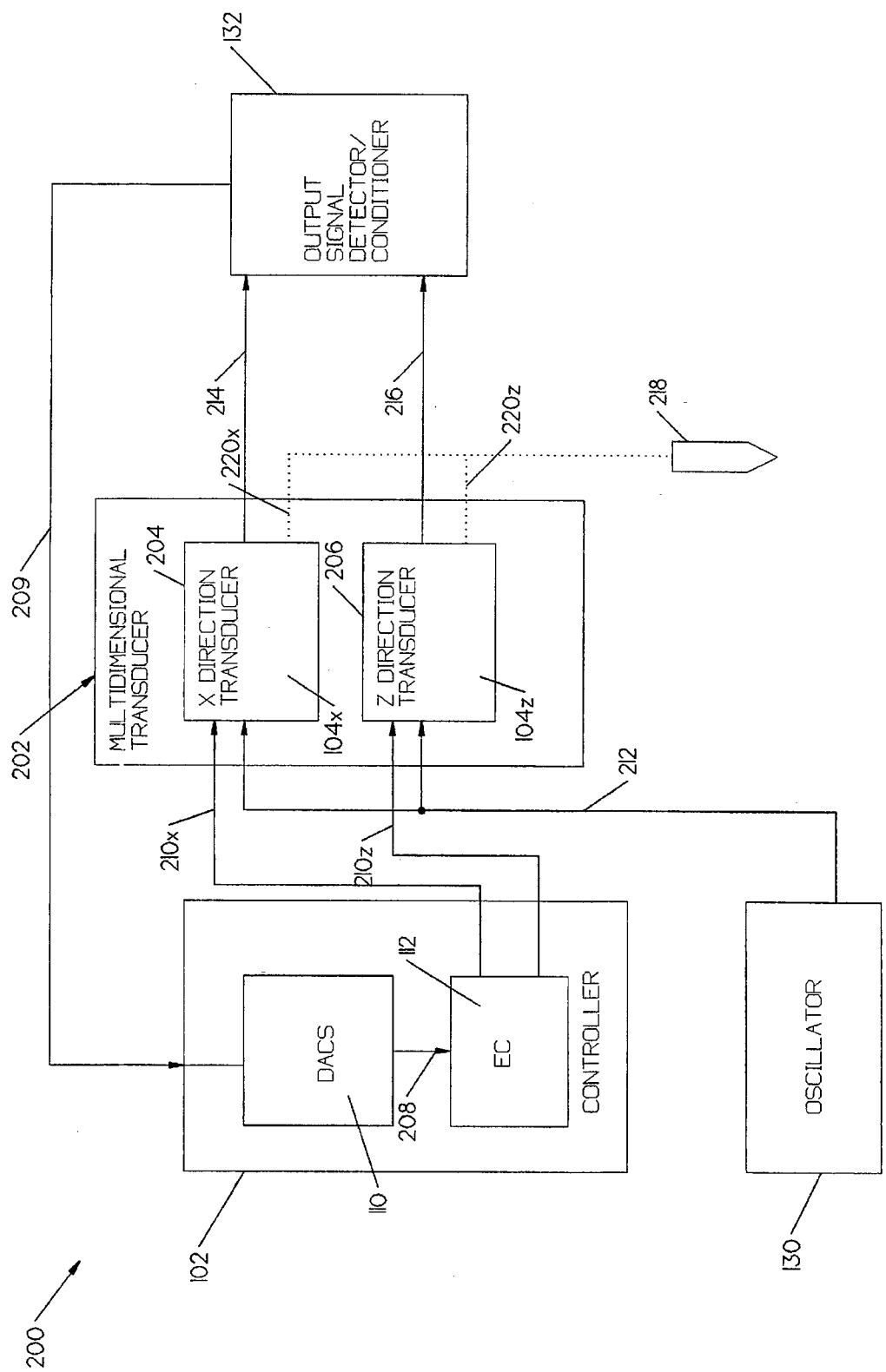
FIG. 5 is a schematic representation incorporating the multi-dimensional transducer of the present invention as a force or movement imparting device and/or as a force, weight or displacement measuring device.

FIG. 5 shows another embodiment of the present invention. A force or movement imparting, and/or detecting system 200 incorporating a multi-dimensional transducer 202 is generally shown. The multi-dimensional transducer 202 allows system 200 to impart forces or movement to a remote object or location, and/or detect forces or position in multiple directions.

In one preferred embodiment shown in FIG. 5, multi-dimensional transducer 202 is a 2-dimensional transducer. Multi-dimensional transducer 202 includes a first or x-direction transducer 204 for imparting or detecting force/movement in a first direction, and a second or z-direction transducer 206 for detecting or imparting force/movement in a second direction. X-direction transducer 204 and z-direction transducer 206 can be similar to the capacitive transducers previously described herein, and in a preferred embodiment, include a multi-plate capacitor transducer 104 (labeled 104x or 104z), which can be similar to the multi-plate capacitor transducer 104 previously described herein, including a pair of drive plates fixedly mounted within transducer 104, and a common pick-up plate moveably mounted within transducer 104 relative to the drive plates.

System 200 includes controller 102, oscillator 130, multi-dimensional transducer 202, and output signal conditioner/detector 132. In general, controller 102 is coupled to multi-dimensional transducer 202 for imparting a force and/or movement output to a location/object remote from multi-dimensional transducer 202 (for example, remote object 218 as shown). Oscillator 130 and output signal conditioner/detector 132 are coupled to multi-dimensional transducer 202 for monitoring the transducer 202 output, which is proportional to force, weight or displacement imparted and/or detected by multi-dimensional transducer 202.

Controller 102 includes data acquisition and control system 110 (DACS) electrically coupled to electrostatic controller 112 (EC), indicated at 208, and coupled to output signal detector/conditioner 132, indicated at 209. Electrostatic controller 112 is coupled to multi-dimensional transducer 202, indicated at 210x and 210z.

Oscillator 130 is electrically coupled to multi-dimensional transducer 202, indicated at 212. Multi-dimensional transducer 202 is electrically coupled to output signal detector/conditioner 132. Specifically, x-direction transducer 204 is coupled to output signal detector/conditioner 132 (at 214) and z-direction transducer 206 is coupled to output signal detector/conditioner 132 (at 216). Multi-dimensional transducer 202 is mechanically coupled to remote object 218, indicated at 220x and 220z dashed lines).

Multi-dimensional transducer 202 may be selectively controlled to impart movement/force of separate magnitude in each direction. Similarly, multi-directional transducer 202 may independently sense force or position in the x-direction or z-direction.

In operation, electrostatic controller 112 selectively applies a relatively high voltage to a drive plate of the multi-dimensional transducer. In one embodiment, the electrostatic controller 112 selectively applies a relatively high voltage to a drive plate of x-direction transducer 204 (at 210x). The electrostatic attraction between the x-direction transducer moveable mounted pick-up plate and fixed drive plate pulls the pick-up plate closer to the drive plate. When the pick-up plate is moved closer to the drive plate, a force or movement transmitting mechanism transmits a corresponding force or movement to remote object 218, indicated by mechanical link 220x. The above-described operation results in remote object 218 being moved or having a force imparted upon remote object 218 in the x-direction.

Similarly, electrostatic controller 112 can selectively apply a relatively high voltage to a drive plate of z-direction transducer 206 (at 210z), which is independent from the voltage applied to x-direction transducer 204. The electrostatic attraction between the moveably mounted pick-up plate of z-direction transducer 206 and the fixed drive plate pulls the pick-up plate closer to the drive plate. When the pick-up plate is moved closer to the drive plate, corresponding force or movement is transmitted to remote object 218. The resulting force or movement imparted upon remote object 218 is in the z-direction, indicated at 220z.

As previously described herein, electrostatic controller 112 may be manually or automatically controlled through data acquisition and control system 110. Data acquisition and control system 110 may be responsive to an output signal 209 from output signal detector/conditioner 132 for selectively varying the voltage applied by electrostatic controller 112, indicated by input 208. Alternatively or additionally, data acquisition and control system 110 can independently control the output 210 of electrostatic controller 112. Data acquisition and control system 110 may be used to log data points received through output signal 209 from output signal detector/conditioner 132.

Oscillator 130 applies a carrier signal to multi-dimensional transducer 202 for providing output signals 214 and 216 which are proportional to force, weight and/or position detected in each direction. Specifically, oscillator 130 provides an AC carrier or high frequency signal to x-direction transducer 204, and x-direction transducer 204 provides output signal 214 to output signal detector/conditioner 132 which is proportional to force, weight and/or position detected (or imparted) by x-direction transducer 204 in the x-direction. Similarly, oscillator 130 provides an AC carrier or high frequency signal to z-direction transducer 206, and z-direction transducer 206 provides output signal 216 to output signal detector/conditioner 132 which is proportional to force, weight and/or position detected (or imparted) by z-direction transducer 206 in the z-direction. Output signal detector/conditioner 132 provides signal 209 to data acquisition and control system 110 which may correspond to signal 214 and/or signal 216.

Multi-dimensional transducer 202 is a 2-dimensional transducer which may impart force on a remote object in two directions, and/or alternatively may detect force or position in two directions. It is recognized that x-direction transducer 204 and z-direction 206 may be independently used as force, weight or position imparting and/or detecting transducers. For example, in one preferred embodiment, electrostatic controller 112 only provides a voltage to z-direction transducer 206 for selectively imparting force or movement to remote object 218. In one embodiment, the voltage is a DC voltage of up to 600 volts for imparting a force of up to 10 mN. Oscillator 130 simultaneously applies a carrier signal to x-direction transducer 204 and z-direction transducer 206 for detection of forces on remote object 218 in the x-direction and in the z-direction. Z-direction transducer 206 provides an output signal 216 to output signal detector/conditioner 132 representative of the force or movement imparted upon remote object 218, and subsequently the detected z-direction forces. X-direction transducer 204 provides an output signal 214 to output signal detector/conditioner 132 representative of the detected x-direction forces.

Figure 7:
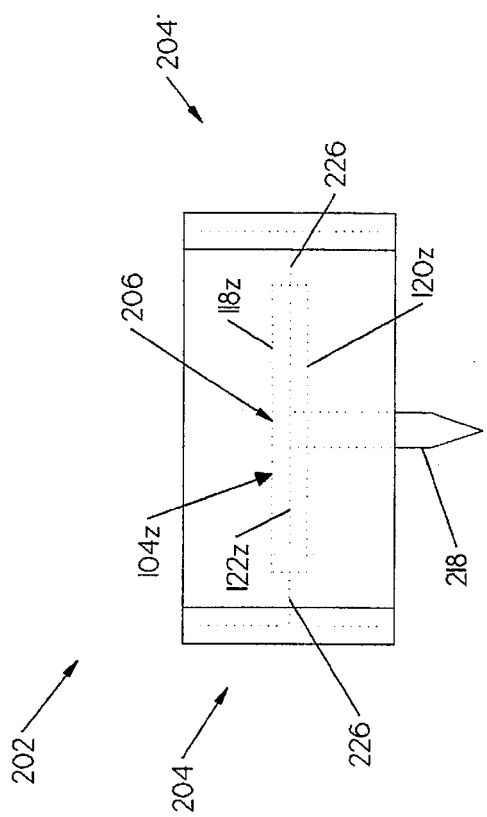
FIG. 7 is a side view of the structural embodiment of the present invention shown in FIG. 6.
Figure 6:
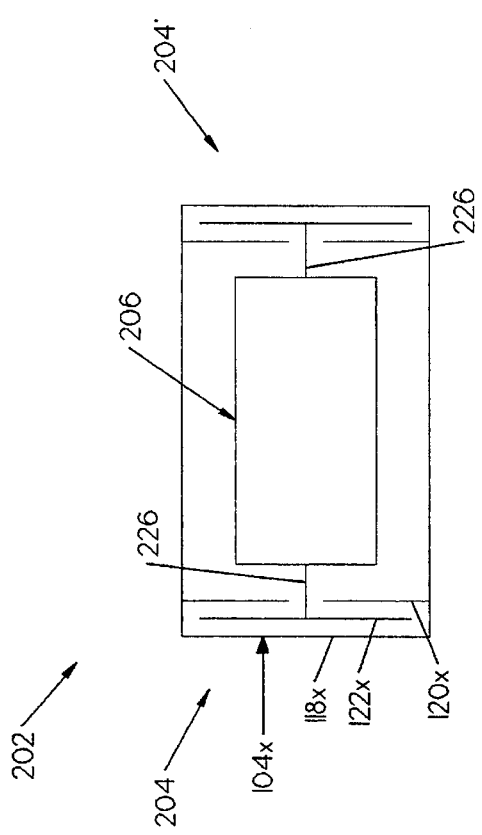
FIG. 6 is a top view of one structural embodiment of the multi-dimensional transducer shown in FIG. 5.

Referring to FIGS. 6 and 7, one preferred structural embodiment of multi-dimensional transducer 202 as a 2-dimensional transducer is generally shown. FIG. 6 is a top view, and FIG. 7 is a side view of multi-dimensional transducer 202. Multi-dimensional transducer 202 is shown mechanically coupled to a remote object 218.

Referring to FIG. 6, x-direction transducer 204 is generally shown, which includes a multi-plate capacitive transducer 104x having drive plate 118x, drive plate 120x, and pick-up plate 122x.

X-direction transducer 204 is mechanically coupled to z-direction transducer 206 through mechanical link 226. Similarly, z-direction transducer 206 includes a multi-plate capacitive transducer 104z, including drive plates 118z and 120z and pick-up plate 122z. Multi-dimensional transducer 202 may independently impart forces on remote object 218 in the x-direction and the z-direction through selective electrostatic actuation of the x-direction transducer 204 and electrostatic actuation of z-direction transducer 206. Similarly, multi-dimensional transducer 202 may detect force and/or movement in the x-direction and z-direction. Additionally, a second x-direction x-direction transducer 204' is included for mechanical stability.

Figure 8:
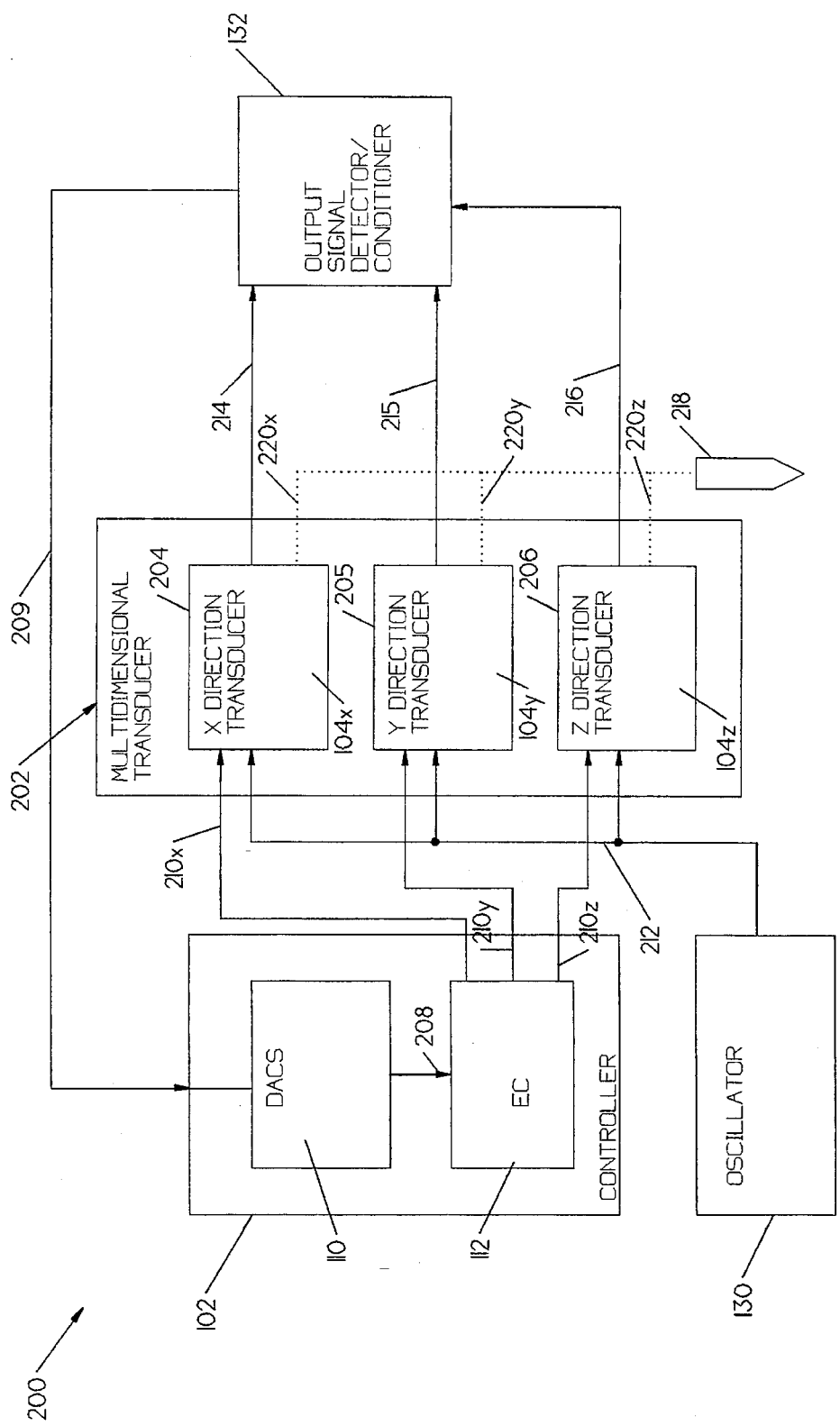
FIG. 8 is a schematic representation of another embodiment incorporating the multi-dimensional transducer of the present invention as a force or movement imparting device and/or as a force, weight or displacement measuring device.

Referring to FIG. 8, yet another embodiment of the present invention is shown, including multi-dimensional transducer 202 within force or movement imparting/detecting system 200. Multi-dimensional transducer 202 further includes a transducer 205 for imparting force or movement and/or for detecting force or movement in a third or y-direction. Y-direction transducer 205 is similar to the capacitive transducers previously described herein, and in a preferred embodiment, includes a multi-plate capacitive transducer 104 (labeled as 104y) as previously described herein.

Electrostatic controller 112 is electrically coupled to y-direction transducer 205 (at 210y). Y-direction transducer 205 is electrically coupled to output signal detector/conditioner 132 (at 215). Additionally, y-direction transducer 205 is mechanically coupled to remote object 218 (at 220y).

Multi-dimensional transducer 202 allows force to be imparted on remote object 218 in three directions and/or provides movement of remote object 218 in three directions. Additionally, oscillator 130 provides a carrier signal 212 to multi-dimensional transducer 202, including x-direction transducer 204, y-direction transducer 205, and z-direction transducer 206, for providing output signals 214, 215, and 216 to output signal detector/conditioner 132 which are proportional to force, weight or position detected in each respective direction.

Referring to FIGS. 9 and 10, one preferred structural embodiment of multi-dimensional transducer 202 as a three-dimensional transducer is shown generally at 230. The preferred structural configuration of multi-dimensional transducer 202 is similar to the structural embodiment of the two-dimensional transducer shown in FIGS. 6 and 7, and further includes third direction or y-direction transducer 205. Similar to x-direction transducer 204 and z-direction transducer 206, y-direction transducer 205 includes a multi-plate capacitive transducer 104y having drive plate 118y, drive plate 120y, and pick-up plate 122y. Y-direction transducer 205 is mechanically coupled to x-direction transducer 204 through mechanical link 227. Y-direction transducer 205 allows the multi-dimensional transducer 202 to detect or impart force and movement in a third or y-direction.

In this embodiment, a second x-direction transducer 204' and a second y-direction transducer 205' are included for mechanical stability. Transducer 204' and transducer 205' function similar to transducer 204 and transducer 205.

Figure 11B:
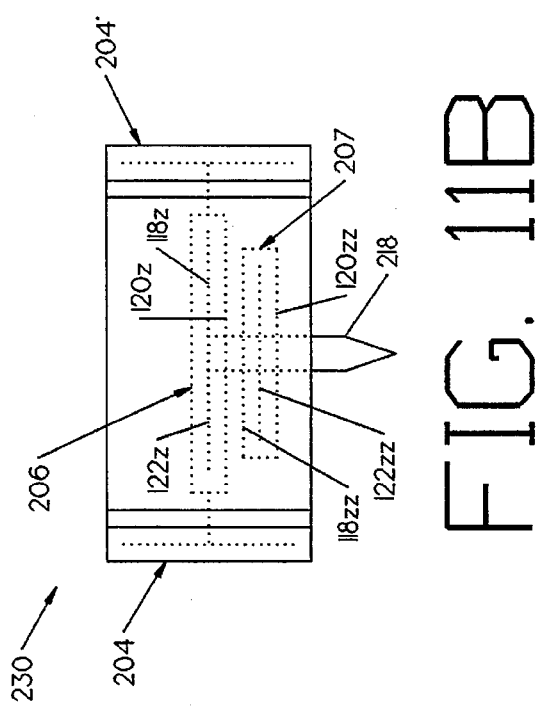
FIG. 11B is a side view of one structural embodiment of the multi-dimensional transducer in accordance with the present invention shown in FIG. 11A.
Figure 11A:
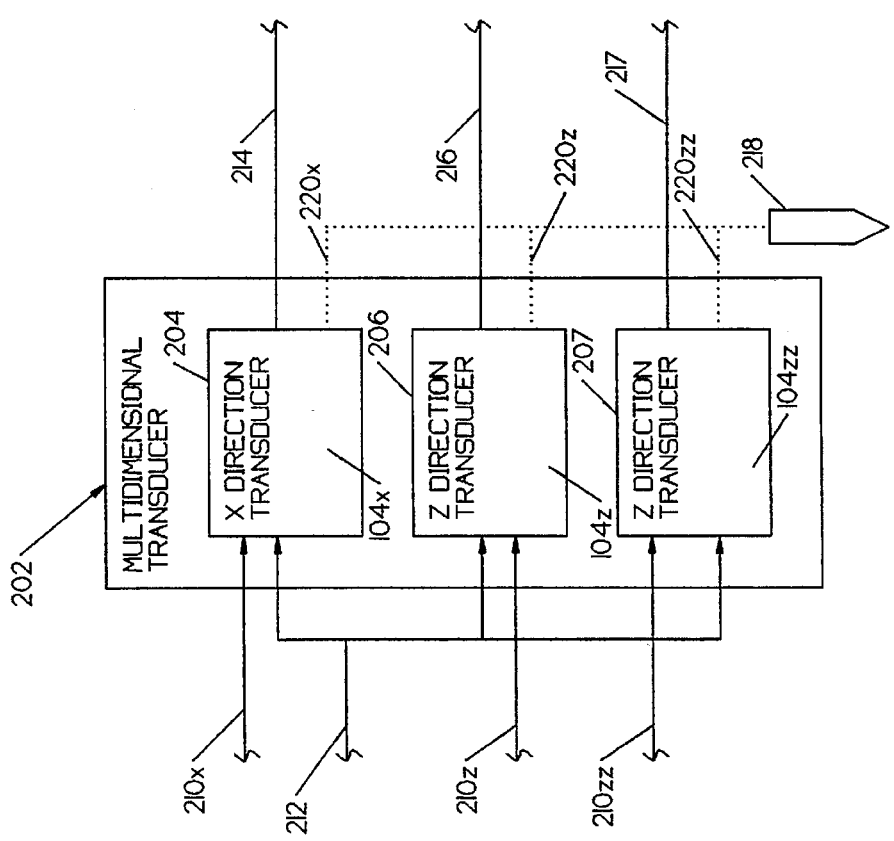
FIG. 11A is yet another schematic representation incorporating the multi-dimensional transducer of the present invention as a force or movement imparting device and/or as a force, weight or displacement measuring device.

It is recognized that multi-dimensional transducer 202 may include additional transducers in either the x-direction, y-direction or z-direction for imparting and/or detecting force/movement. For example, FIGS. 11A and 11B show multi-dimensional transducer 202 as a two-dimensional transducer which includes an additional second or z-direction transducer 207. In the embodiment shown, oscillator 130 (not shown) is coupled to x-direction transducer 204, z-direction transducer 206, and z-direction transducer 207 (at 212). Controller 102 (not shown) is coupled to z-direction transducer 207 (at 210). X-direction transducer 204 (at 214), z-direction transducer 206 (at 216), and z-direction transducer 207 (at 217) are electrically coupled to output signal detector/conditioner 132 (not shown). X-direction transducer 204 (at 220x), z-direction transducer 206 (at 220z), and z-direction transducer 207 (at 220zz) are mechanically coupled to remote object 218.

In operation, x-direction transducer 204 senses lateral forces or movement on remote object 218 in the x-direction, and provides output signal 214 to output signal detector/conditioner 132 which is representative of the forces detected. Z-direction transducer 206 and Z-direction transducer 207 sense forces applied to remote object 218 in the z-direction, and provide corresponding output signal 216 and output signal 217 to output signal detector/conditioner 132 representative of the forces detected on remote object 218 in the z-direction. Additionally, z-direction transducer 206 and z-direction transducer 207 are electrostatically controlled through input signal 210z and input signal 210zz, respectively, for applying an output force (at 220z and/or 220zz) on remote object 218 in the z-direction, and provides output signal 216 and/or output signal 217 to output signal detector/conditioner 132 representative of the displacement of remote object 218.

Yet another embodiment of the present invention is shown in FIGS. 11C and 11D, which includes multi-dimensional transducer 202 having an additional z-direction transducer 207. In this embodiment, x-direction transducer 204, y-direction transducer 205, z-direction transducer 206, and z-direction transducer 207 sense or detect forces on remote object 218 in the respective x, y or z direction. Additionally, transducer 202, through transducers 204, 205, 206 and 207 may selectively impart force or movement to remote object 218 in their respective directions.

Figure 12:
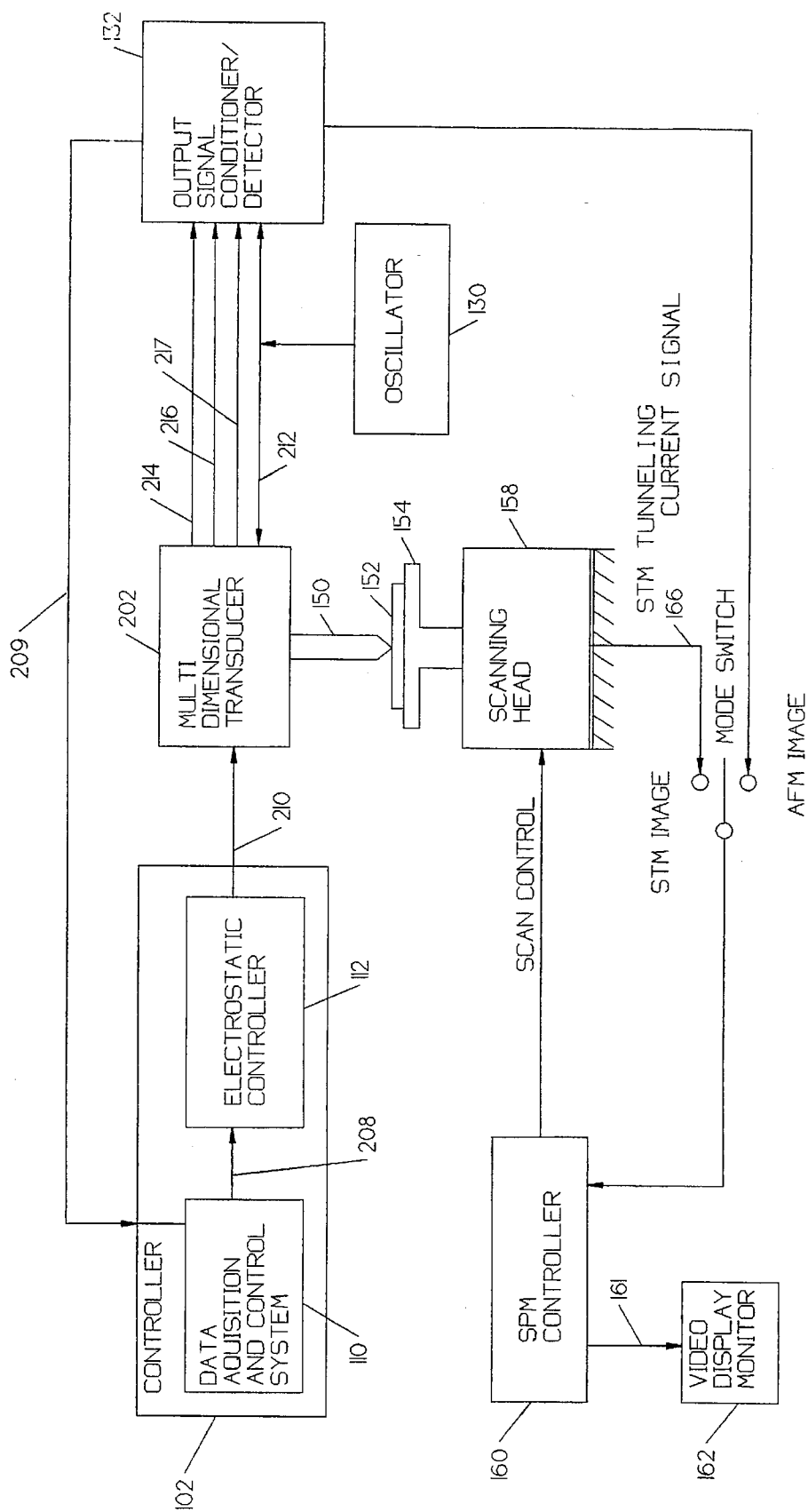
FIG. 12 is a schematic representation of a micro-mechanical test system incorporating the multi-dimensional transducer of the present invention.

Referring to FIG. 12, a schematic representation of a micro-mechanical testing apparatus which may be used for hardness testing and surface imaging incorporating the above-described multi-dimensional transducer 202 of the present invention is depicted. With this embodiment, in situ imaging is possible. A scan of the surface topography of a sample is conducted, followed immediately by the desired micro-mechanical testing, followed by a second imaging of the surface topography using the same instrument. The micro-mechanical test conducted may include indentation, scratch testing, or similar procedure.

The apparatus of applicant's present invention for micro-indentation with subsequent surface imaging utilizes the previously described scanned probe microscope, shown in FIG. 4, with several modifications. The scanning head 158 (which in one preferred embodiment may include a 3-D piezo actuator) is mounted in a fixed position. The sample platform 154 is coupled to the scanning head 158. The sample 152 is positioned on the sample platform 154. The multi-dimensional transducer 202 is coupled to probe 150, which is positioned above sample 152.

In one preferred embodiment, multi-dimensional transducer 202 is a two-dimensional transducer which can be similar to the multi-dimensional transducer 202 shown in FIGS. 11A and 11B, as previously described herein. Multi-dimensional transducer 202 can sense or detect forces in the x-direction using x-direction transducer 204, and in the z-direction using z-direction transducer 206 and/or z-direction transducer 207, and imparts forces on a remote object 218 (in the drawing shown as probe 150) in the z-direction using z-direction transducer 206 and/or z-direction transducer 207.

In use, the surface of sample 152 is imaged as previously described herein using SPM controller 160 coupled to video display monitor 162 (at 161). Scanning head 158 moves the sample 152 back and forth in a raster pattern for imaging the sample surface using methods previously described herein.

Multi-dimensional transducer 202 of Applicant's invention is used for applying force for indentation or scratching, measuring the applied force during indentation or scratching and for imaging before and after testing. Once an image of the sample 152 surface has been made using the above procedure, multi-dimensional transducer 202 is used for forcing the tip of probe 150 into the sample 152 to produce an indentation. Multi-dimensional transducer 202 provides an output signal 217 to output signal conditioner/detector 132 representative of the tip penetration into the sample during the indenting process.

In a preferred embodiment, to perform an indentation, controller 102 (including electrostatic controller 112) is manipulated to selectively apply a voltage to multi-dimensional transducer 202 (at 210), for electrostatic actuation of multi-dimensional transducer 202 to force the probe 150 tip into sample 152. Specifically, in the indentation mode, z-direction transducer 207 is electrostatically actuated transferring a corresponding force to probe 218 in the z-direction, for forcing the probe 150 tip into sample 152. During indentation, z-direction transducer provides an output signal 217 to output signal conditioner/detector 132 representative of the tip penetration into sample 152 and the characteristics of the sample 152 being tested.

The force provided by multi-dimensional transducer 202 for indentation may be selectively controlled by manual operation of electrostatic controller 112, or through automatic operation of electrostatic controller 112 by data acquisition and control system 110. Data acquisition and control system 110 may include a microprocessor or similar logic based system for calculating the voltage to apply to generate a desired force from transducer 202. Alternatively or additionally, data acquisition and control system 110 may be used to log data received from output signal conditioner/detector 132.

Data acquisition and control system 110 may be used to adjust the force applied by multi-dimensional transducer 202 to compensate for movement of the sample as indentation occurs, which is known to occur in softer samples. The force provided by transducer 202 may also be changed by output signal conditioner/detector 132 based on the output signal received from transducer 202. Multi-dimensional transducer 202 further includes x-direction transducer 204 for measuring lateral forces on sample 152 (output indicated at 214).

After indentation, the sample 152 surface can then be reimaged with the same tip so that the result of the indentation test can be seen in minutes, rather than hours, without the need for moving the sample or finding the point where the indentation was made in the sample. Further, because the first image, indentation, and second image are all made with the sample in a single position, it is assured that the first surface image and second surface image are of the same surface area and show the corresponding effect of the indentation step.

In the imaging mode, z-direction transducer senses/detects forces on remote object 218 (probe 150 in FIG. 12) in the z-direction, and provides output signal 217 to output signal conditioner/detector 132 representative of the force detected. Additionally, in the imaging mode, z-direction transducer 206 may be used as a positioning transducer as an alternative to using scanning head 158. Z-direction transducer 206 takes over the function of positioning in the z-direction. Z-direction transducer 206 operates as a positioning transducer in a feedback loop to maintain the position in the z-direction of probe 218 (shown as tip 150 in FIG. 12) relative to the surface of sample 152.

Figure 13A:
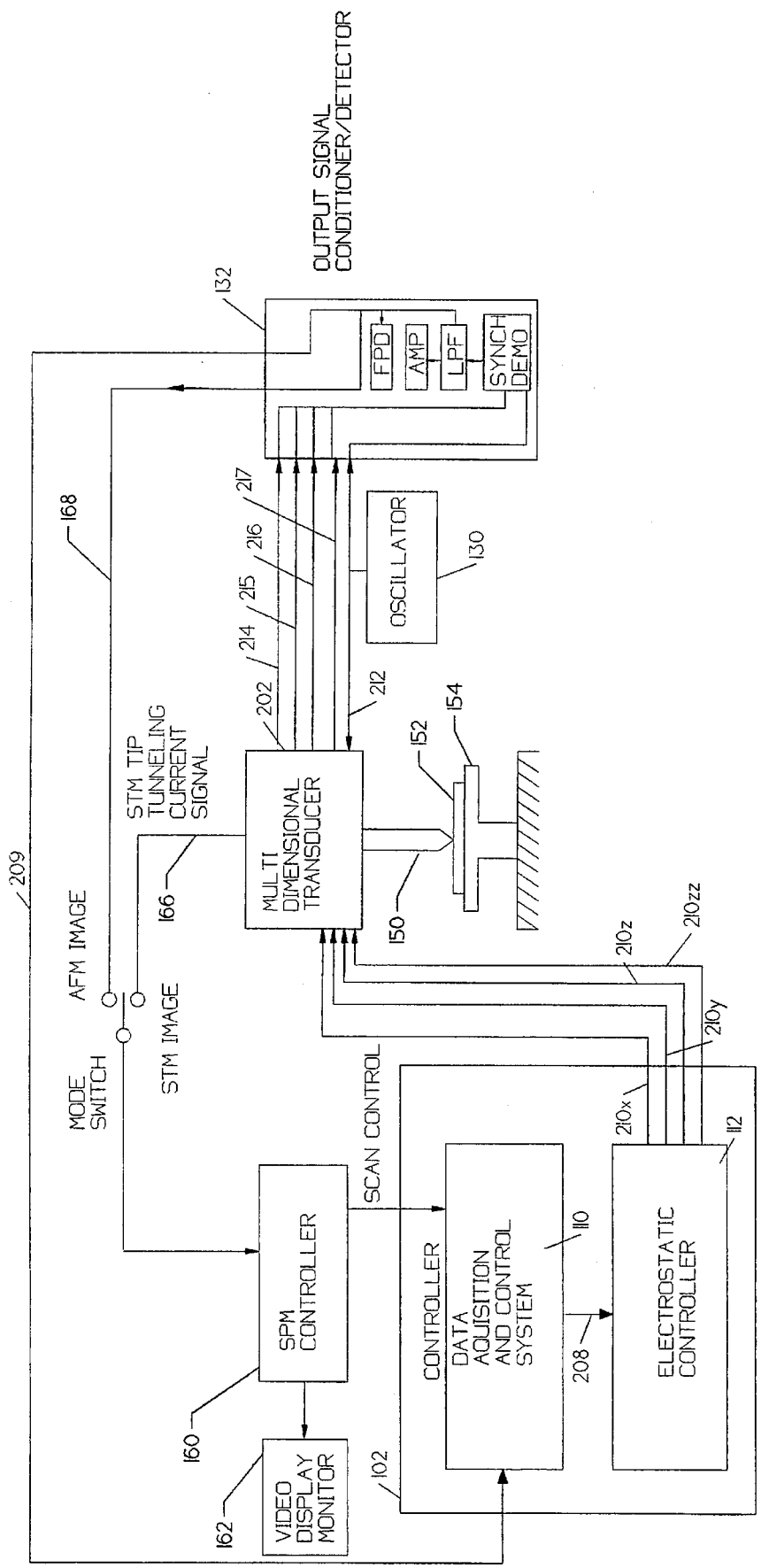
FIG. 13A is another schematic representation of a micro-mechanical test system incorporating the multi-dimensional transducer of the present invention.

Referring to FIG. 13A, yet another embodiment of a micro-mechanical testing apparatus using the multi-dimensional transducer of the present invention is shown. In one preferred embodiment, multi-dimensional transducer 202 is similar to the multi-dimensional transducer shown in FIGS. 11C and 11D as previously described herein. During surface imaging, multi-dimensional transducer 202 is used to scan the tip of probe 150 back and forth in a raster pattern over the surface of sample 152, for imaging the sample surface. Additionally, multi-dimensional transducer 202 is used for controlling the tip of probe 150 for performing the desired micro-mechanical test which may include performing an indentation or scratch in sample 152. After indentation, the sample 152 can again be imaged with the same tip so that the results of the indentation or scratch test can be imaged immediately after performing the test. In each of these modes, multi-dimensional transducer 202 is used for moving, positioning, providing force or sensing/detecting forces in the multiple directions.

As shown in FIG. 13A, in one preferred embodiment, output signal conditioner/detector 132 includes a synchronous demodulator coupled to a low pass filter (LPF). The low pass filter is coupled to an amplifier (AMP) for conditioning of output signal 203 received from multi-dimensional transducer 202. Additionally, a front panel display (FPD) may be coupled to the amplifier for providing an output display representative of output signals 214, 215, 216 and 217.

Figure 13B:
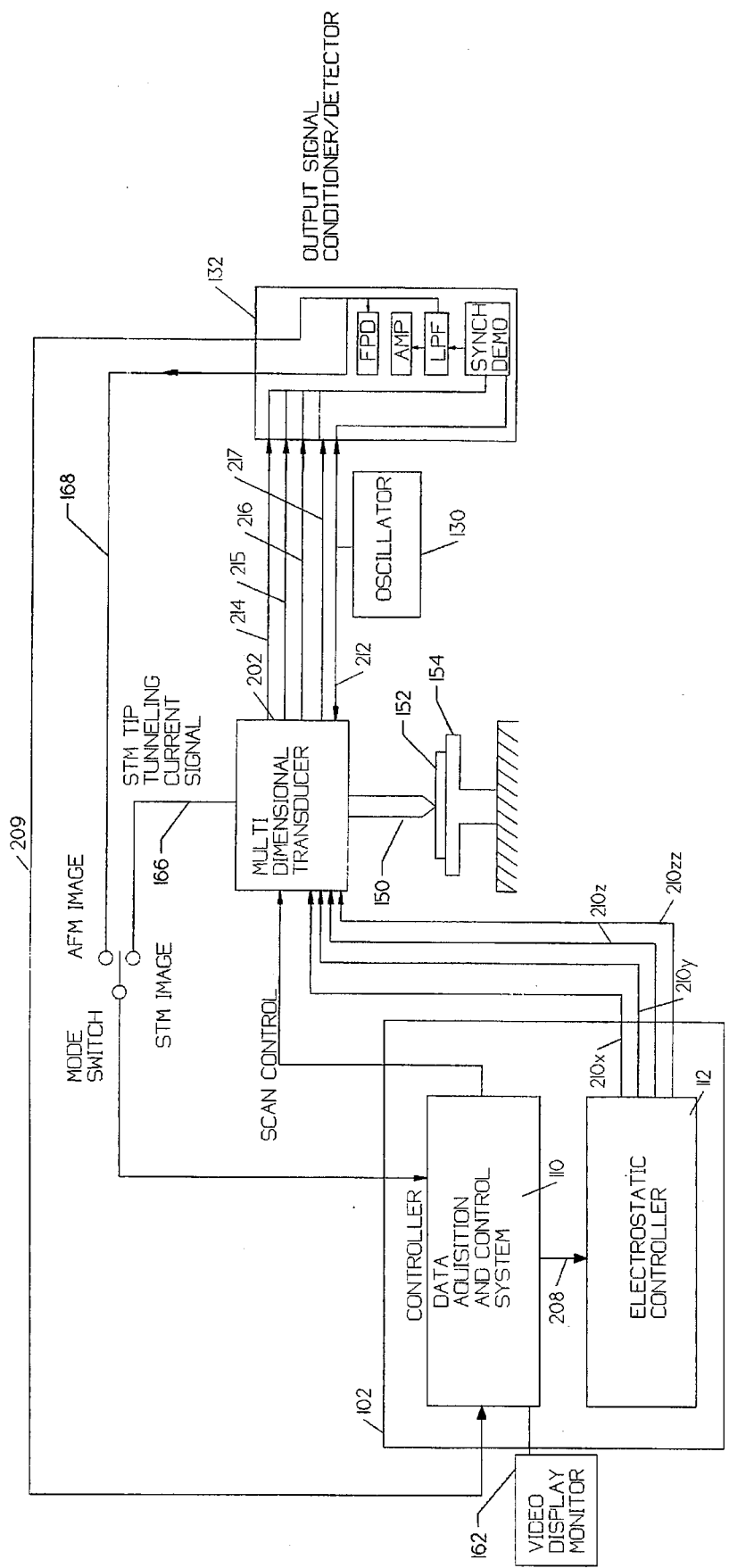
FIG. 13B is another schematic representation of a micro-mechanical test system incorporating the multi-dimensional transducer of the present invention.

Referring to FIG. 13B, a micro-mechanical testing apparatus using the multi-dimensional transducer of the present invention is shown, which can be similar to the micro-mechanical testing apparatus shown in FIG. 13A. In this embodiment, a stand-alone system is shown with controller 102 performing the previous functions of SPM controller 160.

When the transducer of the present invention is used with a scanned probe microscope with its own scanner (typically a piezo scanner), the microscope scanner can be used to withdraw the sample from the probe, allowing the transducer output to be set to zero periodically. This is required to compensate for thermal drift. When the multi-dimensional transducer 202 performs the functions of the scanning head (158), rather than work in conjunction with it, some means must be provided to allow for periodic drift compensation. It is recognized that one possible method would be to use a stepper motor driving a screw to withdraw the probe from the sample, but that method may disturb the x and y position if done while an image is being scanned.

In one preferred embodiment, the means of compensating for drift is to use two z-axis transducers (such as z-direction transducer 206 and z-direction transducer 207). One z-direction transducer may be used as the positioning device, responding to the feedback signal from the second z-direction transducer to maintain a constant contact force. Correction for drift can be done at any time by withdrawing the first z-direction transducer slightly, so the tip mounted on the second z-direction transducer is no longer contacting the sample, and resetting the output to zero with an offset adjust circuit. Since there is no sideways play in the z-direction transducers, this procedure can be done at any time without disturbing the position of the probe (218) relative to the sample, even in the middle of scanning an image.

Figure 14:
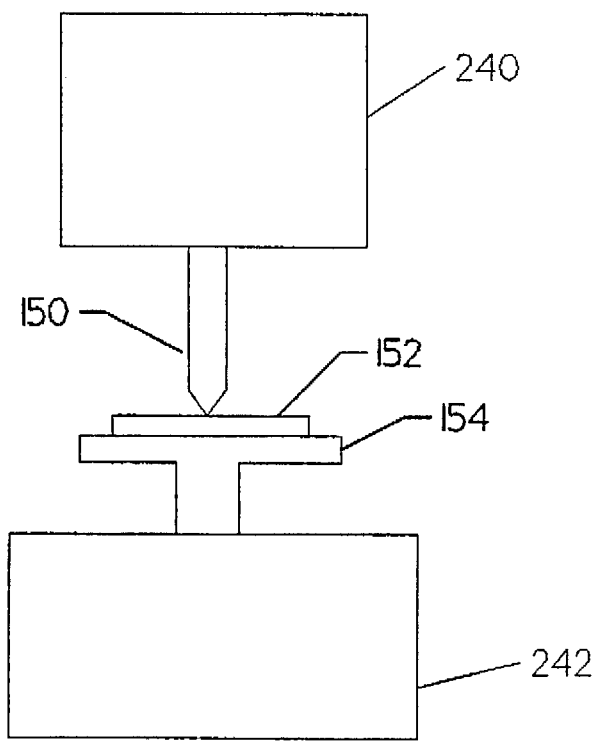
FIG. 14 is a schematic representation showing alternative mounting configurations of a micro-mechanical test system incorporating the multi-dimensional capacitive transducer of the present invention.

Referring to FIG. 14, it is recognized that alternative mounting configurations may be used between multi-dimensional transducer 202 and probe 150 for testing sample 152 for use in a scan probe microscope test system. As shown, box 240 may include a multi-dimensional transducer 202, and box 242 may be a fixed surface similar to that shown in FIG. 12. Alternatively, box 240 may be a fixed surface, and box 242 may include multi-dimensional transducer 202. Additionally, it is recognized that box 240 or box 242 may include a scanning head mechanically coupled to a scanned probe microscope apparatus for performing various operations during a micro-mechanical test procedure.

Figure 15:
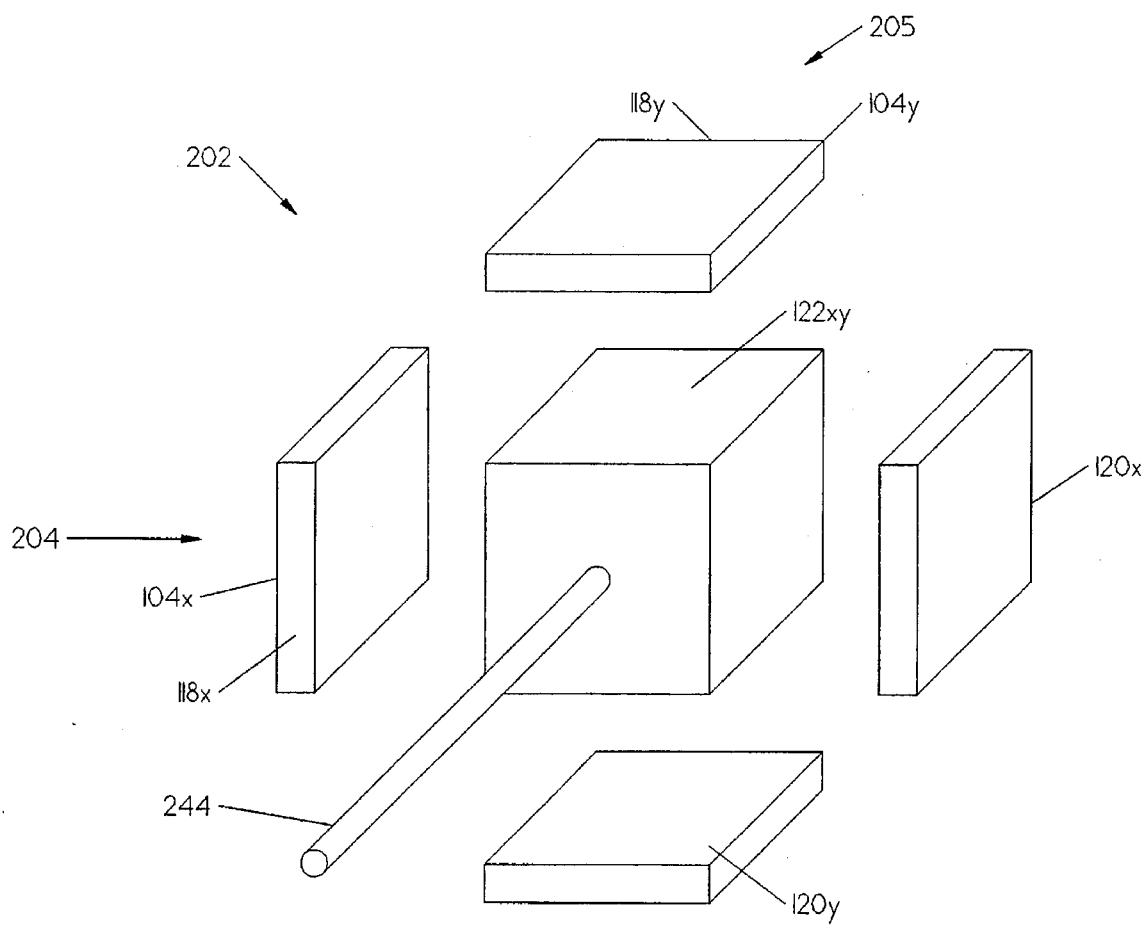
FIG. 15 is yet another alternative structural embodiment of the multi-dimensional transducer in accordance with the present invention.

It is also recognized that multi-dimensional transducer 202 may take on alternative structural embodiments while still remaining in the scope of the present invention. For example, referring to FIG. 15, a two-dimensional multi-dimensional transducer 202 is shown which includes an x-direction transducer 204 and a y-direction transducer 205. In this embodiment, x-direction transducer 204 includes capacitive transducer 104x having drive plates 118x and 120x, having a common center plate 122xy which is also common to y-direction transducer 205. Y-direction transducer 205 capacitive transducer 104x also includes drive plates 118y and 120y. Center plate 122xy is moveably mounted between drive plates 118x, 118y, 120x, and 120y. Mechanism 244 is coupled to center plate 122xy for movement of center plate 122xy. One application for this structural embodiment of multi-dimensional transducer 202 is for use as a computer mouse or "joystick".

Figure 16:
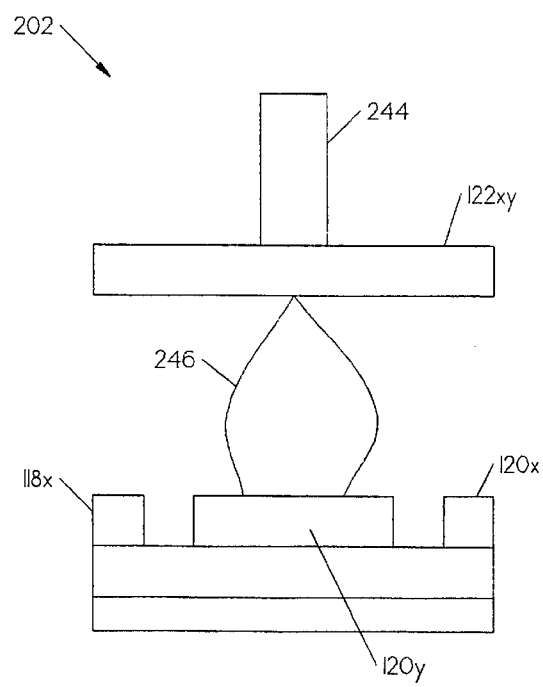
FIG. 16 is a side view of yet another alternative structural embodiment of the multi-dimensional transducer in accordance with the present invention.
Figure 17:
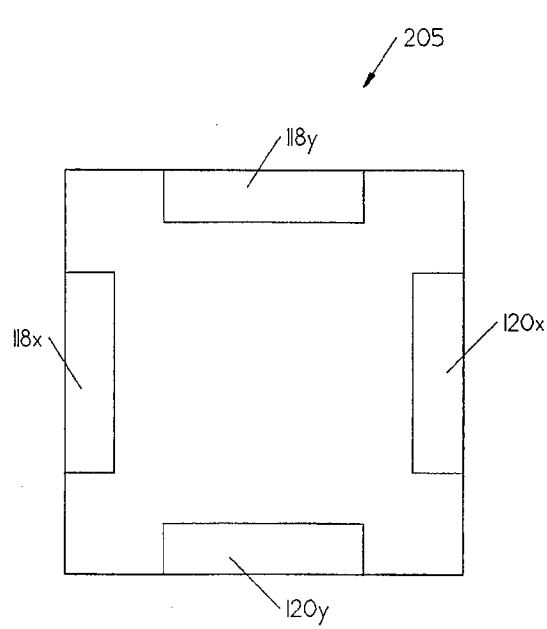
FIG. 17 is a top view of the multi-dimensional transducer shown in FIG. 16.

Referring to FIGS. 16 and 17, yet another alternative embodiment of the multi-dimensional transducer 202 of the present invention is shown. In this embodiment, center plate 122xy is moveably mounted above drive plates 118x, 118y, 120x, and 120y using suspension system 246. Mechanism 244 is coupled to center plate 122xy for movement of center plate 122xy relative to drive plates 118x, 118y, 120x, and 120y. One application of this structural embodiment of multi-dimensional transducer 202 is also for use as a computer mouse or "joystick".

The present invention provides the combined capability of nano-micro-mechanical testing and high resolution in situ imaging in a single system. This completely eliminates the effort, time and uncertainty involved with trying to relocate indents in a conventional AFM or SEM after they were produced in a separate indentation instrument as is normally required.

In addition to indentation and hardness testing at the nano scale, the present invention may be used for micro-scratch/ scratch testing, wear testing of materials, such as hard protective coatings, and micro-machining. Wear resistance of materials such as hard protective coatings can be evaluated by repeatedly scanning a region and recording the wear rate at various contact forces. The wear depth can be measured by increasing the scan size after the measurement, to image both the foreign region and the surrounding regional surface. Using this procedure, it has been found possible to measure wear depths as small as 0.2 nm.

The present invention is extremely useful for testing hard coatings on items ranging from eye glasses to magnetic recording disks. Additional applications include micromechanical testing of thin films for micro-electronic integrated circuits, capacitors and pasivation layers. As integrated circuit features become more complex and the number of metalization layers increases, mechanical effects due to mismatches of thermal expansion coefficients and process related stresses become more important. Micromechanical testing of these structures can be used to evaluate the stresses and the probable affect they will have on device reliability using the present invention. Coatings for cutting tools and other mechanical components to increase wear or corrosion resistance can also be evaluated using the present invention.

With the present invention, in situ imaging at the nano meter scale resolution is achieved, allowing measurements to be made which were not previously possible. Very small indents of 100 nm or less diameter have been produced and imaged with the present invention. Previously, indents of this size produced on a separate indentor would be nearly impossible to locate later using a microscope (100 nm features would require a scan size on the order of 1 µm for imaging. If the sample could be repositioned with a total error of 100 µm (0.004 inches), there are 10,000 possible 1 µm regions that the indent could be located in.) Even with larger indents or other features placed on the sample to aid in location, these small indents cannot be reliably located once the sample is moved.

At very small loads, indents have been produced in both GaAs and single crystal copper that are not stable, returning to the original flat surface within a short period of time. Surfaces having this type of behavior would be impossible to study on conventional micro/nano indentors, as the indent would have disappeared long before it could be located in a microscope for inspection.

Additionally, it is recognized that the micro-machining capabilities of the present invention can be used for experimental modification of magnetic recording heads to trim-track widths or alter air bearing surfaces. Other applications include exposing varied metalization layers in integrated circuits to allow probing of signals for debugging or failure analysis.

If imaging is not required, it is possible to operate the present invention as a conventional micro-indentor, with the instrument providing load/displacement curves at a fraction of the cost of other micro/nano indentors.

New characteristics and advantages of the invention covered by this document have been set forth in the foregoing description. It will be understood, however, that this disclosure is, in many ways, only illustrative. Changes may be made in details, particularly in matters of shape, size, and arrangement of parts, without exceeding the scope of the invention. The scope of the invention is, of course, defined in the language in which the appended claims are expressed.

What is claimed:

1. A high precision multi-dimensional transducer comprising:
    a first capacitive transducer including means for imparting force or movement and/or detecting force, weight, or position in a first direction via a pick-up plate movably mounted relative to a drive plate therein; and
    a second capacitive transducer including means for imparting force or movement and/or detecting force, weight, or position in a second direction via a pick-up plate movably mounted relative to a drive plate therein.

2. The transducer of claim 1, further wherein each transducer includes means for transmitting force between an object remote from each pick-up plate and said pick-up plate.

3. The transducer of claim 2, further comprising means responsive to the position of each pick-up plate relative to the respective drive plate for providing an output signal proportional to said relative position.

4. The transducer of claim 1, further comprising means for selectively controlling each pick-up plate.

5. The transducer of claim 4, wherein the means for selectively controlling each pick-up plate further includes means for selectively imparting a force on the remote object via the pick-up plate.

6. The transducer of claim 5, wherein the means for selectively imparting a force on the remote object via the pick-up plate includes electrostatic actuation.

7. The transducer of claim 4, wherein the means for selectively controlling each pick-up plate includes a controller having an electrostatic actuator coupled to each transducer.

8. The transducer of claim 1, further comprising a third capacitive transducer including means for imparting force or movement and/or detecting force, weight or position in a third direction having a pick-up plate movably mounted therein.

9. A high precision multi-dimensional transducer comprising:

a first capacitive transducer for imparting force or movement and/or detecting force, weight, or position in a first direction having a pick-up plate movably mounted relative to a drive plate therein;

a second capacitive transducer for imparting force or movement and/or detecting force, weight, or position in a second direction having a pick-up plate movably mounted relative to a drive plate therein;

a third capacitive transducer for imparting force or movement and/or detecting force, weight or position in a third direction having a pick-up plate movably mounted therein; and a fourth capacitive transducer for imparting force or movement and/or detecting force, weight or position in the second direction having a pick-up plate movably mounted relative to a drive plate therein.

10. A high precision multi-dimensional transducer comprising:

a first capacitive transducer for imparting force or movement and/or detecting force, weight, or position in a first direction having a pick-up plate movably mounted relative to a drive plate therein;

a second capacitive transducer for imparting force or movement and/or detecting force, weight, or position in a second direction having a pick-up plate movably mounted relative to a drive plate therein; and a third capacitive transducer for imparting force or movement and/or detecting force, weight or position in the second direction having a pick-up plate movably mounted relative to a drive plate therein.

11. A high precision, multi-dimensional transducer comprising:

a first capacitive transducer for detecting force, weight or position in a first direction having a pick-up plate movably mounted relative to a drive plate therein;

a second capacitive transducer for detecting force, weight or position in a second direction having a pick-up plate movably mounted relative to a drive plate therein;

means to couple each pick-up plate to a remote object; and means to generate an output signal proportional to the force, weight or position detected.

12. The transducer of claim 11, further including means for selectively controlling the position of each pick-up plate and/or a force generated by each pick-up plate.

13. The transducer of claim 12, wherein the means for controlling the position and/or force includes electrostatic actuation.

14. The transducer of claim 12, further comprising means for drift compensation in the second direction, including a third transducer similar to the second transducer.

15. The transducer of claim 11, further comprising a third capacitive transducer including means for detecting force, weight or position in a third direction having a pick-up plate movably mounted relative to a drive plate therein.

16. In a scanned probe microscope apparatus, the improvement comprising a high precision multi-dimensional transducer including:

a first capacitive transducer including means for imparting force or movement and/or detecting force, weight or position in a first direction via a pick-up plate movably mounted relative to a drive plate therein; and a second capacitive transducer including means for imparting force or movement and/or detecting force, weight, or position in a second direction via a pick-up plate movably mounted relative to a drive plate therein.

17. The transducer of claim 16, further wherein each transducer includes means for transmitting force between an object remote from each pick-up plate and said pick-up plate.

18. The transducer of claim 17, further comprising means responsive to the position of each pick-up plate relative to the drive plate for providing an output signal proportional to said relative position.

19. The transducer of claim 16, further comprising means for selectively controlling each pick-up plate.

20. The transducer of claim 19, wherein the means for selectively controlling each pick-up plate further includes means for selectively imparting a force on the remote object via the pick-up plate.

21. The apparatus of claim 20, wherein the means for selectively imparting a force on the remote object via the pick-up plate includes electrostatic actuation.

22. The apparatus of claim 19, wherein the means for selectively controlling each pick-up plate includes a controller having an electrostatic actuator coupled to each transducer.

23. The transducer of claim 16, further comprising a third capacitive transducer including means for imparting force or movement and/or detecting force, weight, or position in a third direction having a pick-up plate movably mounted therein.

24. In a scanned probe microscope apparatus, the improvement comprising a high precision multi-dimensional transducer including:

a first capacitive transducer for imparting force or movement and/or detecting force, weight or position in a first direction having a pick-up plate movably mounted relative to a drive plate therein;

a second capacitive transducer for imparting force or movement and/or detecting force, weight, or position in a second direction having a pick-up plate movably mounted relative to a drive plate therein; and a third capacitive transducer for imparting force or movement and/or detecting force, weight, or position in the second direction having a pick-up plate movably mounted therein.

25. A method of performing a micro-mechanical test on a sample comprising the steps of placing the sample, and performing the micro-mechanical test using a high-precision, multi-dimensional capacitive transducer, wherein the step of performing the micro-mechanical test using the multi-dimensional capacitive transducer further comprises the steps of:

imparting force or movement and/or detecting force weight, or position in a first direction; and imparting force or movement and/or detecting force, weight, or position in a second direction.

26. A method of performing a micro-mechanical test on a sample comprising the steps of placing the sample, and performing the micro-mechanical test using a high-precision, multi-dimensional capacitive transducer, wherein the step of performing the micro-mechanical test using the multi-dimensional capacitive transducer further comprises the steps of:

imparting force or movement and/or detecting force, weight, or position in a first direction; and imparting force or movement and/or detecting force, weight, or position in a second direction wherein the step of performing the micro-mechanical test using a high-precision, multi-dimensional capacitive transducer further comprises the step of imparting force or movement and/or detecting force, weight or position in a third direction.

27. In a scanned probe microscope apparatus having a piezo scanner for moving a sample relative to a tip, the improvement comprising:

means for surface imaging and multi-axis force and/or displacement measurement including a multi-dimensional transducer having, a first capacitive transducer including means for detecting force, weight or position in a first direction having a pick-up plate movably mounted relative to a drive plate therein, and a second capacitive transducer including means for detecting force, weight or position in a second direction having a pick-up plate movably mounted relative to a drive plate therein;

means to couple each pick-up plate to a remote object; and means to generate an output signal proportional to the force, weight or position detected.

28. The apparatus of claim 27, further comprising means for providing application of multi-axis force and/or displacement.

29. In a scanned probe microscope apparatus, the improvement comprising:

a multi-dimensional capacitive transducer;

means coupled to the transducer for surface imaging, multi-axis force and/or displacement measurement; and means coupled to the transducer for application of multi-axis force and/or displacement.

30. An instrument for providing high resolution surface imaging and micro-mechanical properties test, the instrument comprising:

a probe;

means for scanning, including providing relative motion between the probe and a sample, the means for scanning including a multi-dimensional transducer; and a controller coupled to the multi-dimensional transducer, including a data acquisition and control system and an electrostatic controller.

31. The instrument of claim 30, further comprising:

a video display monitor coupled to the controller; and a means for operator control coupled to the controller.

32. A high precision multi-dimensional transducer comprising:

a first capacitive transducer including means for imparting force or movement and/or detecting force, weight, or position in a first direction via a pick-up plate movably mounted relative to a drive plate therein;

a second capacitive transducer including means for imparting force or movement and/or detecting force, weight, or position in a second direction via a pick-up plate movably mounted relative to a drive plate therein; and means for mechanically coupling the first capacitive transducer pick-up plate to the second capacitive transducer pick-up plate.

33. The transducer of claim 32, wherein the means for mechanically coupling includes means for maintaining each pick-up plate relatively parallel to its respective drive plate during movement of the pick-up plate.

34. The transducer of claim 32, wherein the means for mechanically coupling moves the first capacitive transducer pick-up plate in the same direction as the second capacitive transducer pick-up plate during movement of each pick-up plate.

* * * * *